(12) United States Patent
Branch et al.

(10) Patent No.: US 6,610,065 B1
(45) Date of Patent: Aug. 26, 2003

(54) INTERBODY FUSION IMPLANTS AND INSTRUMENTATION

(75) Inventors: Charles L. Branch, Advance, NC (US); Mingyan Liu, Bourg-la-Reine (FR); Lawrence M. Boyd, Memphis, TN (US); Loic Josse, Palaja (FR)

(73) Assignee: SDGI Holdings, Inc., Wilmington, DE (US)

( * ) Notice: Subject to any disclaimer, the term of this patent is extended or adjusted under 35 U.S.C. 154(b) by 336 days.

(21) Appl. No.: 09/698,623

(22) Filed: Oct. 27, 2000

Related U.S. Application Data

(62) Division of application No. 09/181,353, filed on Oct. 28, 1998, now Pat. No. 6,174,311.

(51) Int. Cl.[7] .............................................. A61B 17/16
(52) U.S. Cl. ........................................... 606/84; 606/61
(58) Field of Search .............................. 606/79, 84, 85, 606/86, 87, 96, 102, 184, 61; 144/75, 78, 79; 30/167, 168, 167.1, 167.2, 173, 174

(56) References Cited

U.S. PATENT DOCUMENTS

| | | | |
|---|---|---|---|
| 3,486,505 A | 12/1969 | Morrison | |
| 3,848,601 A | 11/1974 | Ma et al. | |
| 4,545,374 A | 10/1985 | Jacobson | |
| 4,714,469 A | 12/1987 | Kenna | |
| 4,736,738 A | 4/1988 | Lipovsek et al. | |
| 4,743,256 A | 5/1988 | Brantigan | |
| 4,834,757 A | 5/1989 | Brantigan | |
| 4,877,020 A | 10/1989 | Vich | |
| 4,878,915 A | 11/1989 | Brantigan | |
| 4,950,296 A | 8/1990 | McIntyre | |
| 5,015,247 A | 5/1991 | Michelson | 606/61 |
| 5,062,845 A | 11/1991 | Kuslich et al. | 606/80 |
| 5,190,548 A | 3/1993 | Davis | 606/80 |
| 5,250,061 A | 10/1993 | Michelson | 606/160 |
| 5,306,309 A | 4/1994 | Wagner et al. | |

(List continued on next page.)

FOREIGN PATENT DOCUMENTS

| | | |
|---|---|---|
| EP | 0 077 159 | 4/1983 |
| EP | 0 307 241 | 3/1989 |
| WO | 95/08306 | 3/1995 |
| WO | 95/15133 | 6/1995 |
| WO | 96/22747 | 8/1996 |
| WO | 96/40013 | 12/1996 |
| WO | 97/13378 | 4/1997 |
| WO | 97/15248 | 5/1997 |
| WO | 97/25945 | 7/1997 |

OTHER PUBLICATIONS

AcroMed Spine Tools "PLIG Instruments" (undated).
"Brantigan I/F Cage Acromed" (undated).
"Brantigan I/F Cage for PLIF" (1991).
Sofamor Danek "Laparoscopic Bone Dowel Surgical Technique" (1995).
Sofamor Danek "Surgical Technique Using Bone Dowel Instrumentation for Posterior Approach", LIT.PLIF.ST96 (1996).
Sofamor Danek "Surgical Tips Posterior Approach" (1998).
University of Florida Tissue Bank, Inc. "Allograft Catalog" (1998).

Primary Examiner—David O. Reip
(74) Attorney, Agent, or Firm—Woodard, Emhardt, Moriarty, McNett & Henry LLP

(57) ABSTRACT

This invention relates to implants formed from donor bone for use in lumbar interbody fusion procedures and instruments for performing such procedures. The implants are formed to include a concave surface formed from a portion of the medullary canal of a long bone. The concaved surface defines a recess in the implant that serves as a depot for osteogenic material. Specific instruments for inserting the implants prepared according to this invention and for preparing the intervertebral space to receive the implants are also provided.

7 Claims, 34 Drawing Sheets

U.S. PATENT DOCUMENTS

| | | |
|---|---|---|
| 5,423,825 A | 6/1995 | Levine ......................... 606/86 |
| 5,423,855 A | 6/1995 | Marienne .................... 606/208 |
| 5,425,772 A | 6/1995 | Brantigan |
| 5,443,514 A | 8/1995 | Steffee |
| 5,445,639 A | 8/1995 | Kuslich et al. ............... 606/80 |
| 5,484,437 A | 1/1996 | Michelson ................... 606/61 |
| 5,489,307 A | 2/1996 | Kuslich et al. |
| 5,499,984 A | 3/1996 | Steiner ....................... 606/80 |
| 5,514,180 A | 5/1996 | Heggeness et al. |
| 5,593,409 A | 1/1997 | Michelson ................... 606/61 |
| 5,609,636 A | 3/1997 | Kohrs et al. |
| 5,645,598 A | 7/1997 | Brosnahan, III |
| 5,669,909 A | 9/1997 | Zdeblick et al. .............. 606/61 |
| 5,709,683 A | 1/1998 | Bagby ......................... 606/61 |
| 5,716,355 A | 2/1998 | Jackson et al. ............... 606/61 |
| 5,720,749 A | 2/1998 | Rupp .......................... 606/79 |
| 5,728,159 A | 3/1998 | Stroever et al. |
| 5,741,253 A | 4/1998 | Michelson ................... 606/61 |
| 5,766,253 A | 6/1998 | Brosnahan, III |
| 5,857,995 A | 1/1999 | Thomas et al. ............... 604/22 |

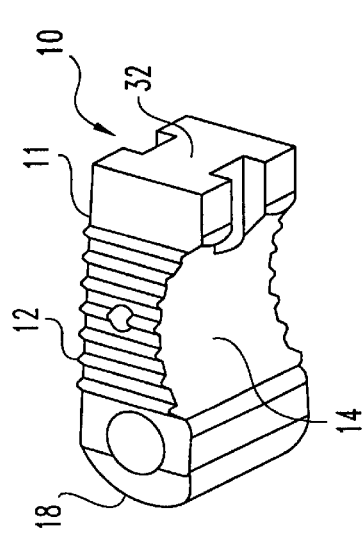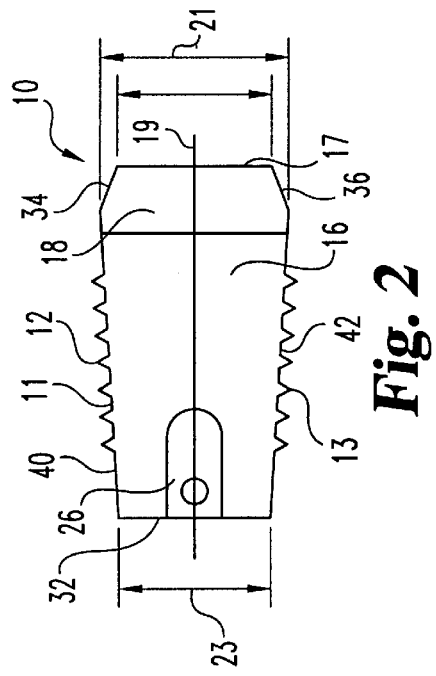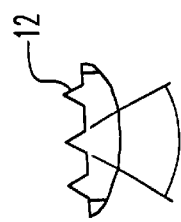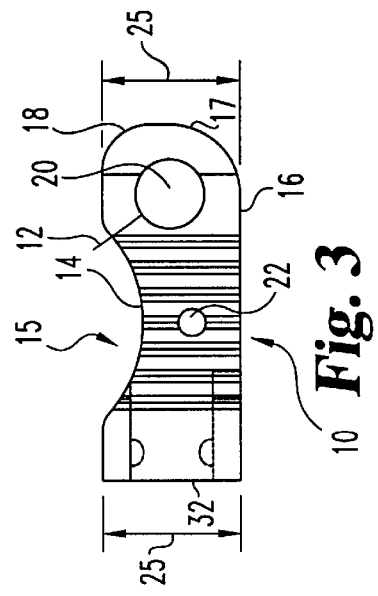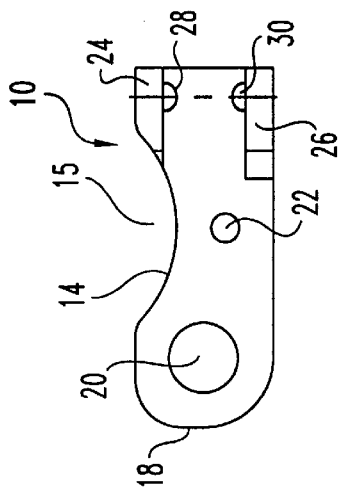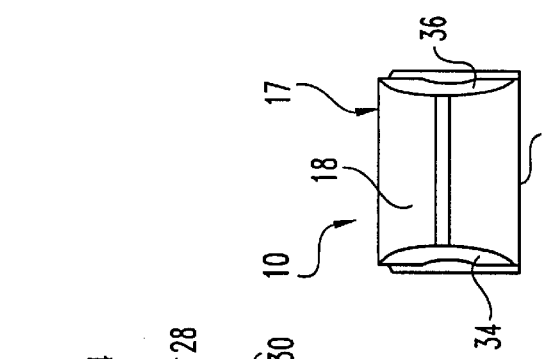

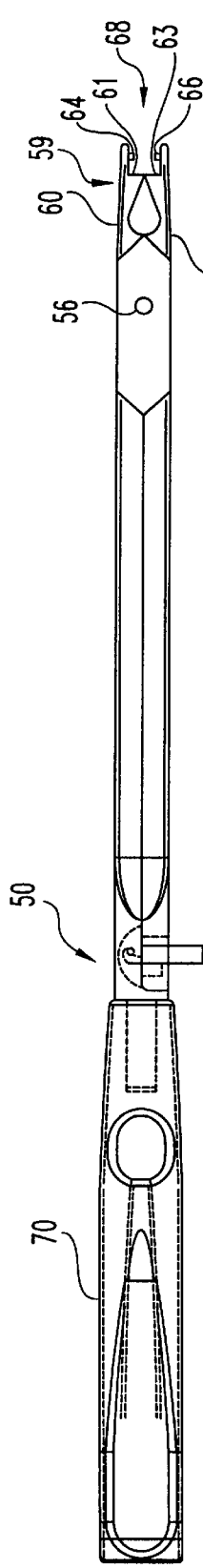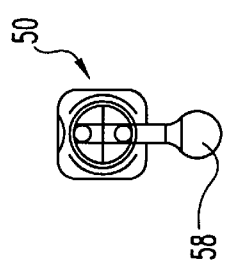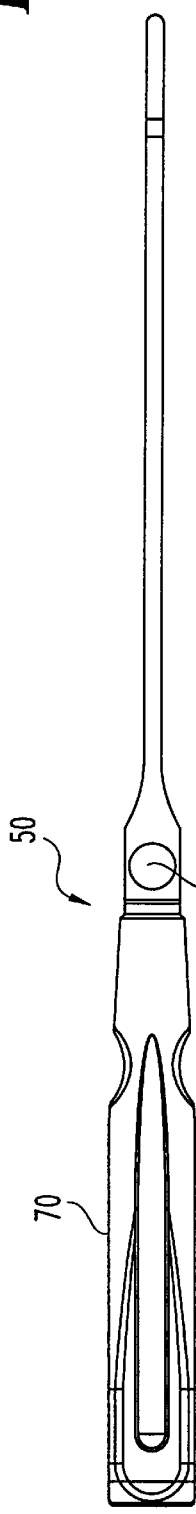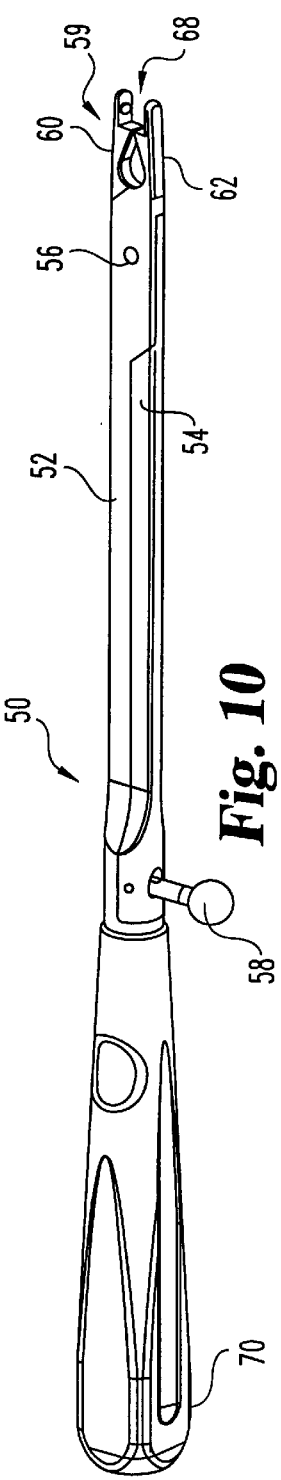

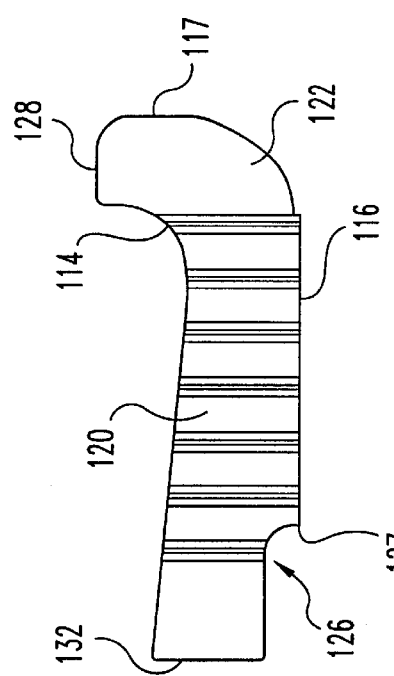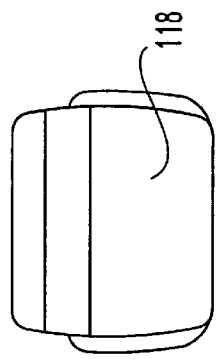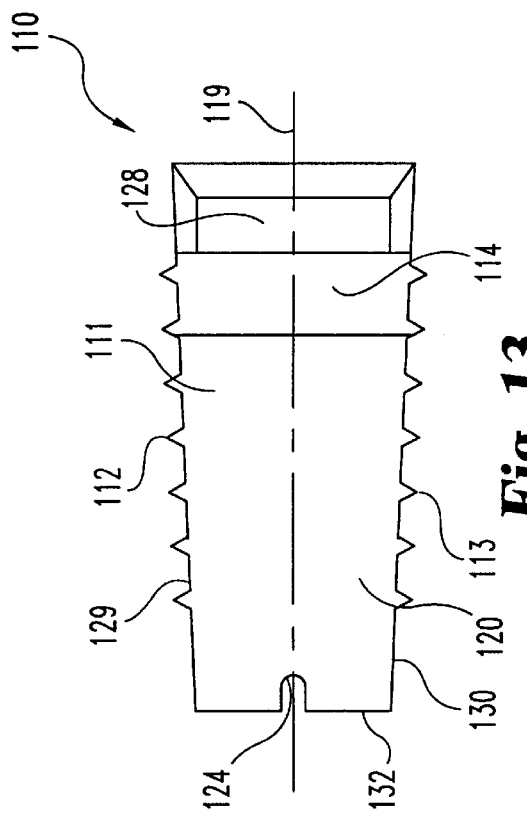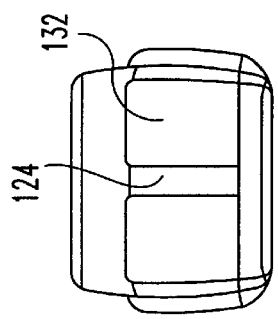

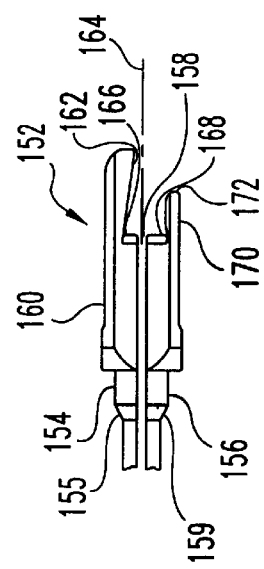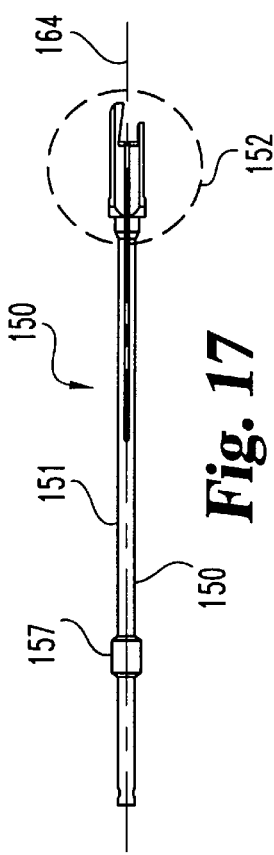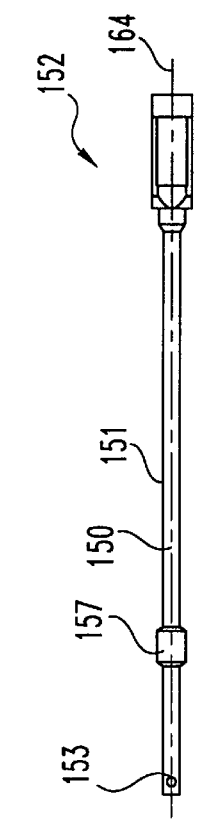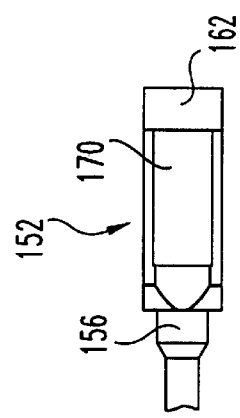

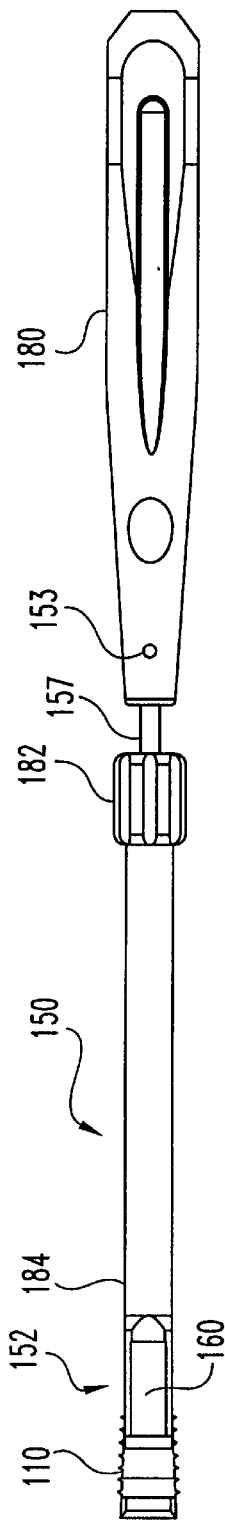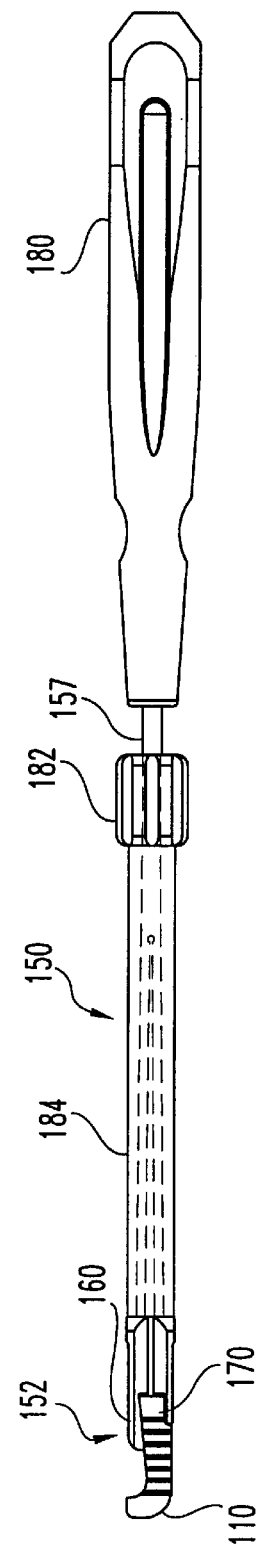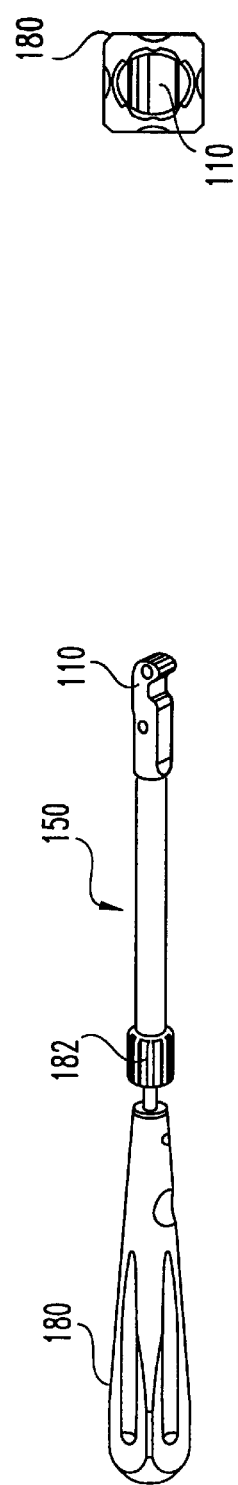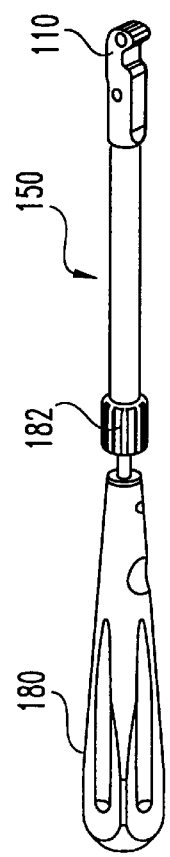

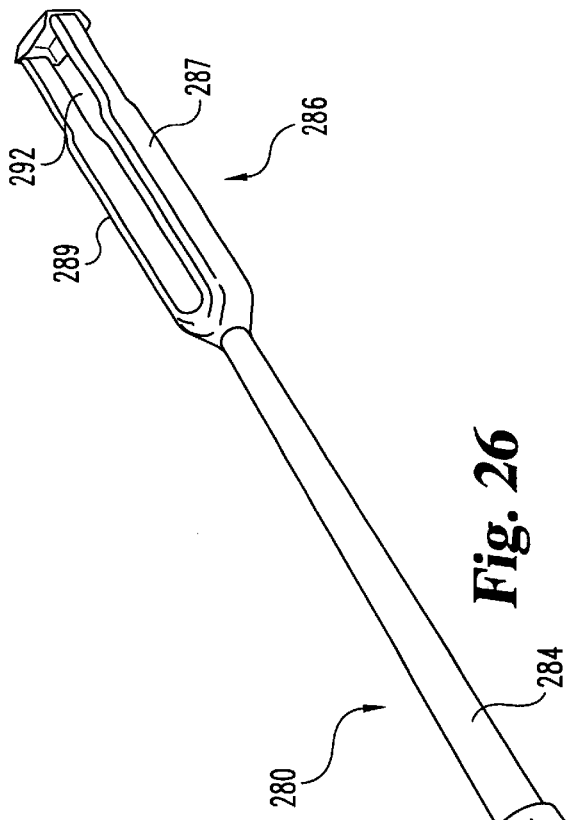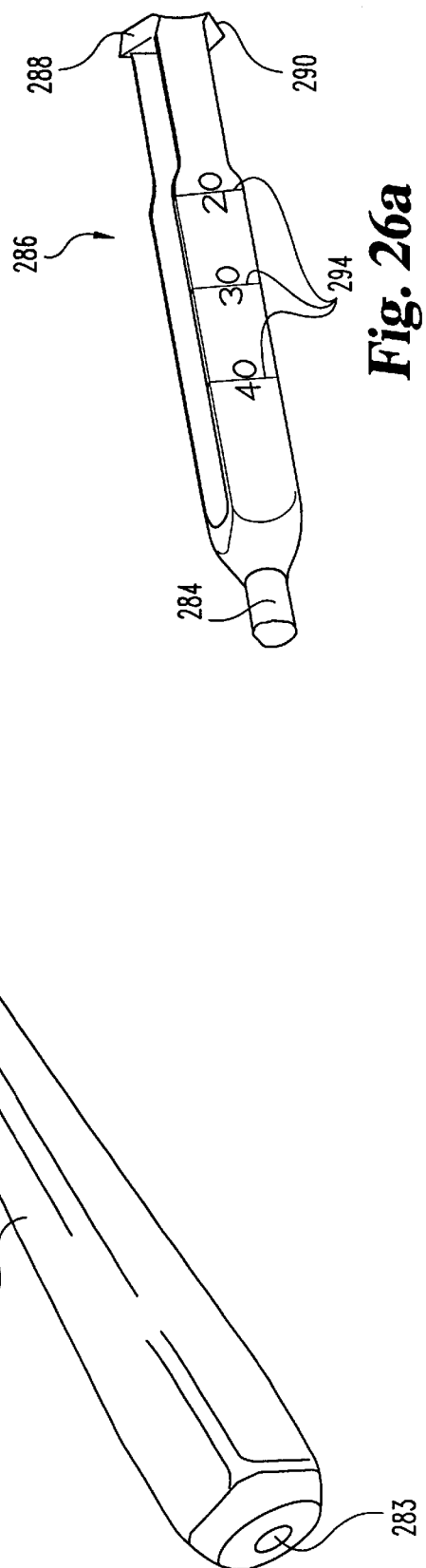

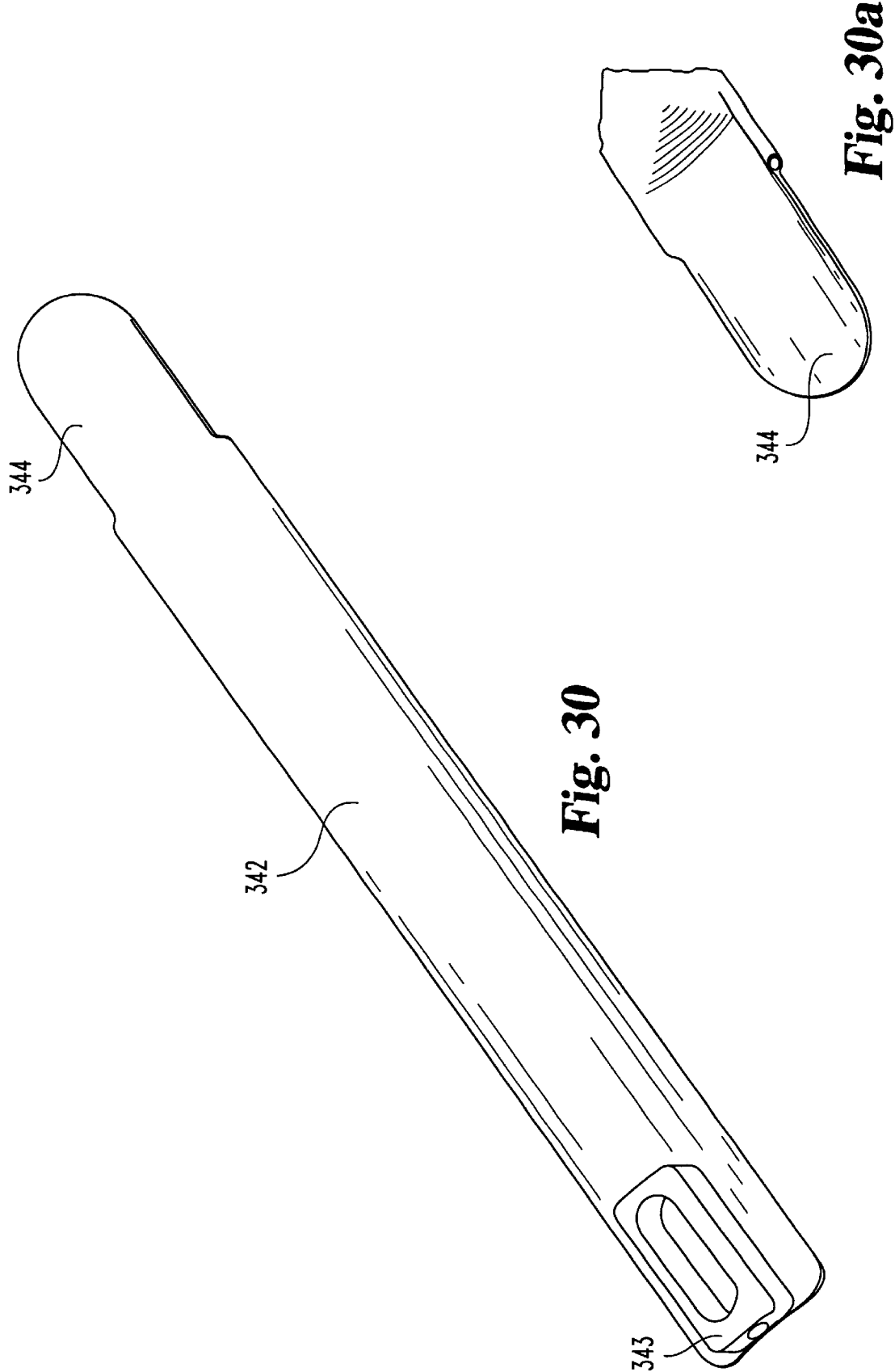

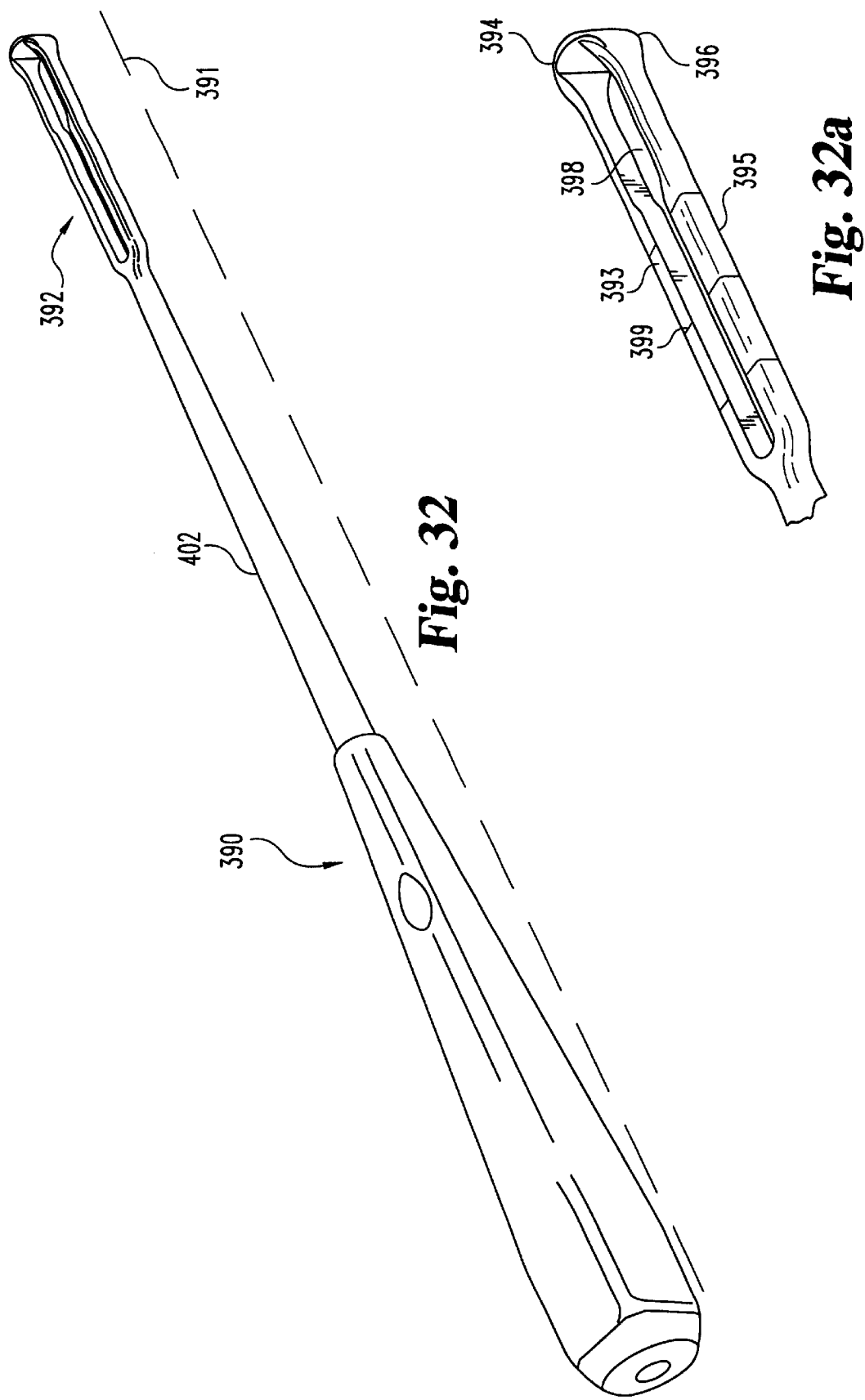

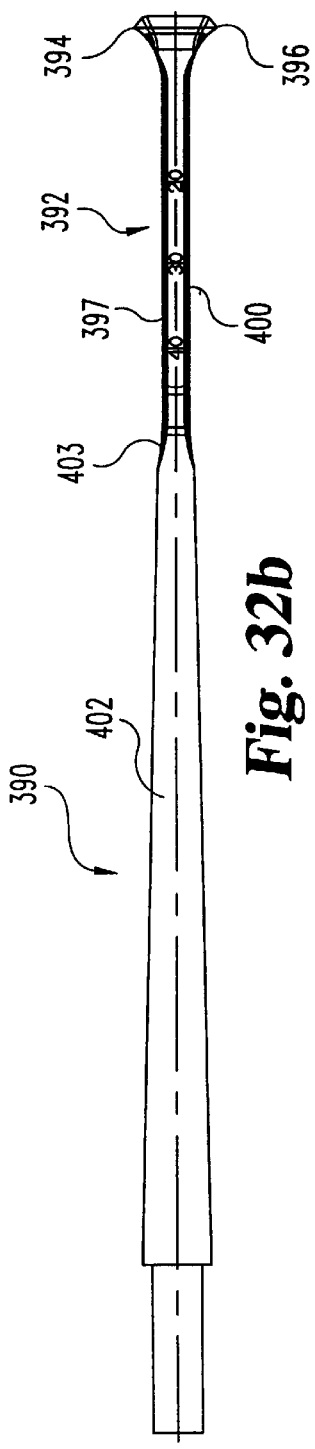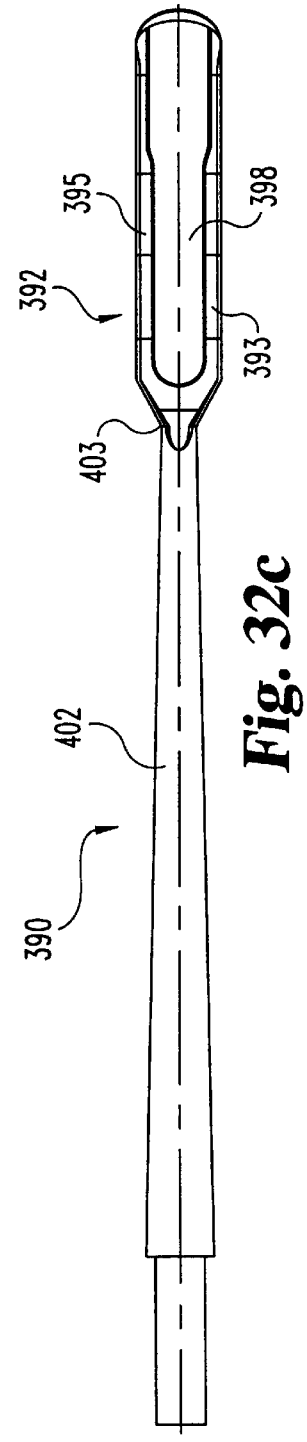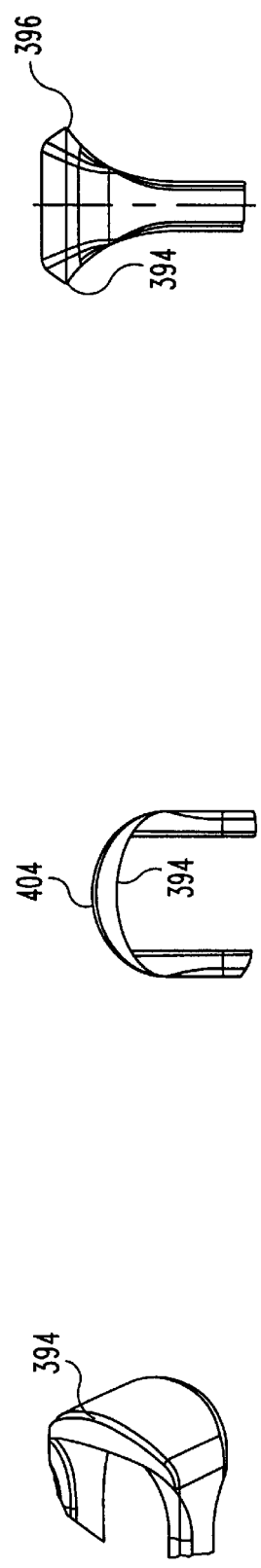
Fig. 32b
Fig. 32c
Fig. 32f
Fig. 32e
Fig. 32d

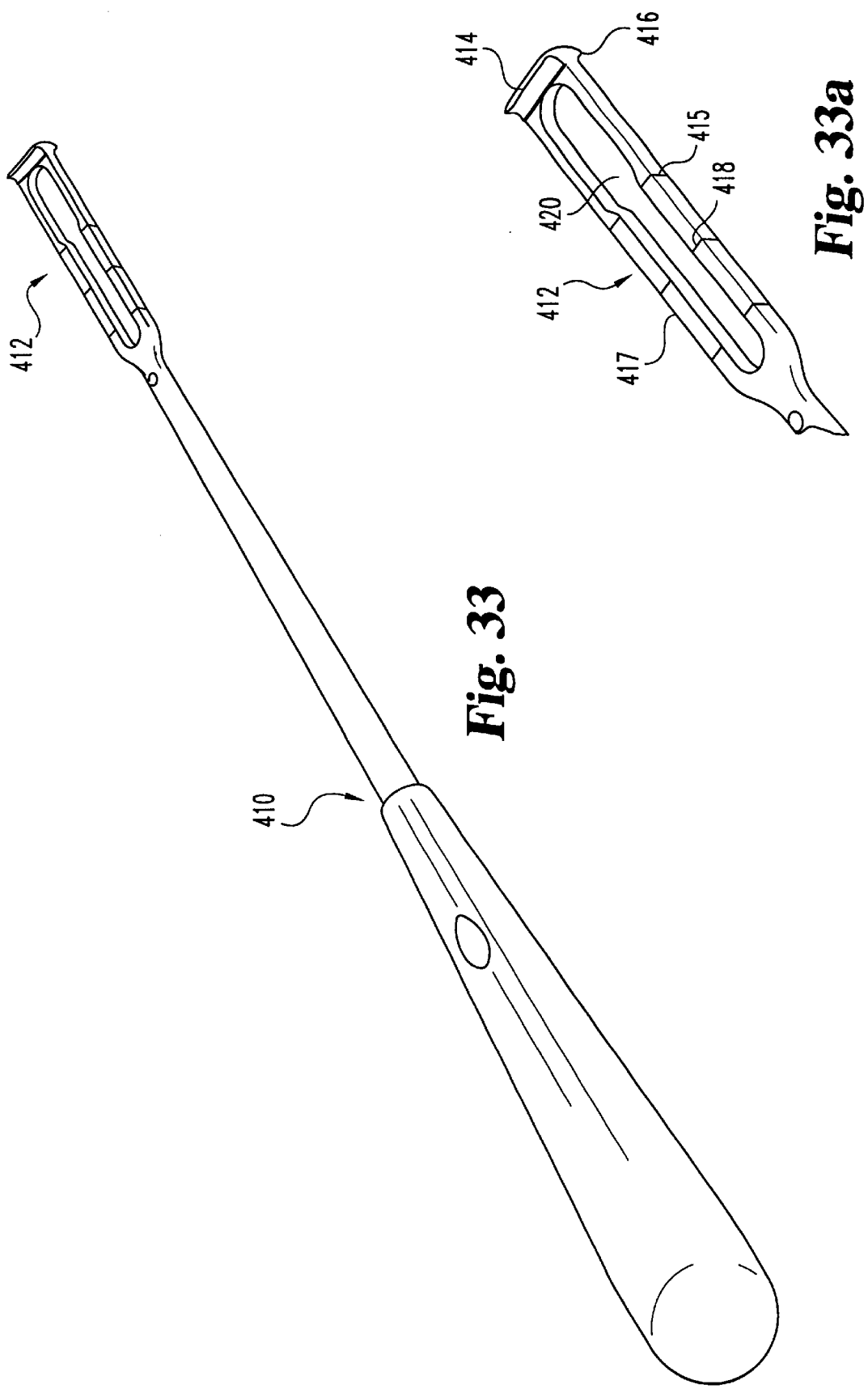

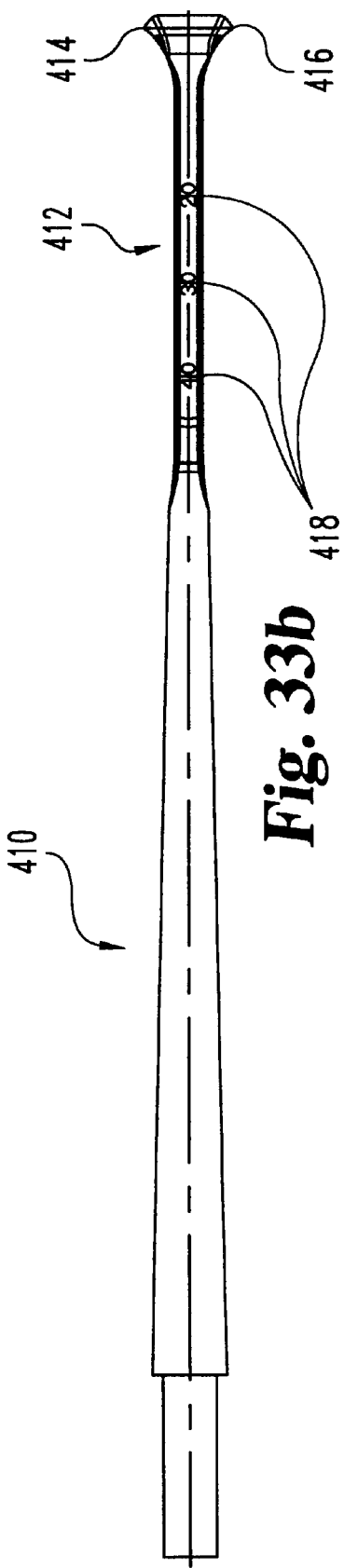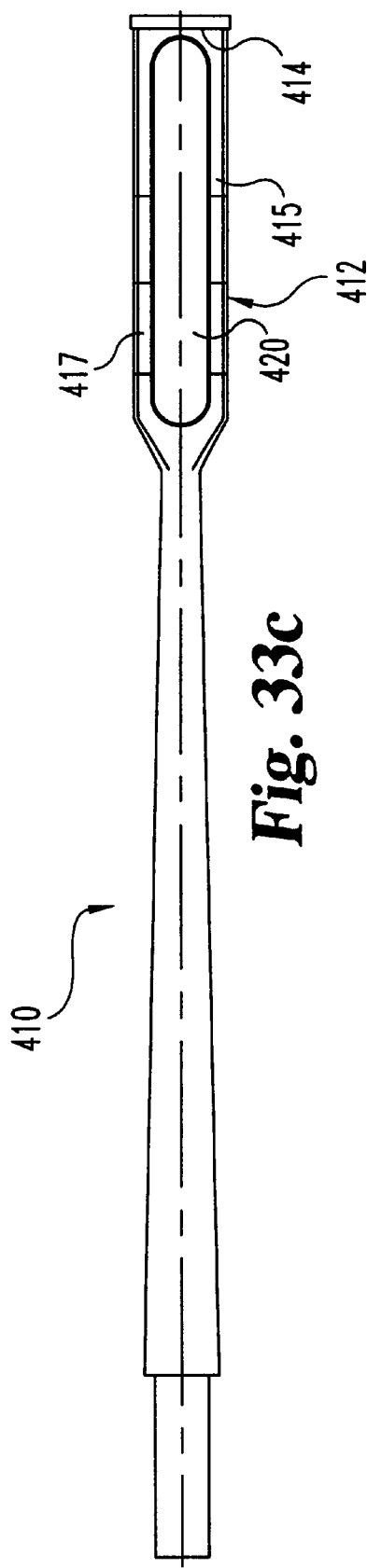
Fig. 33b
Fig. 33c

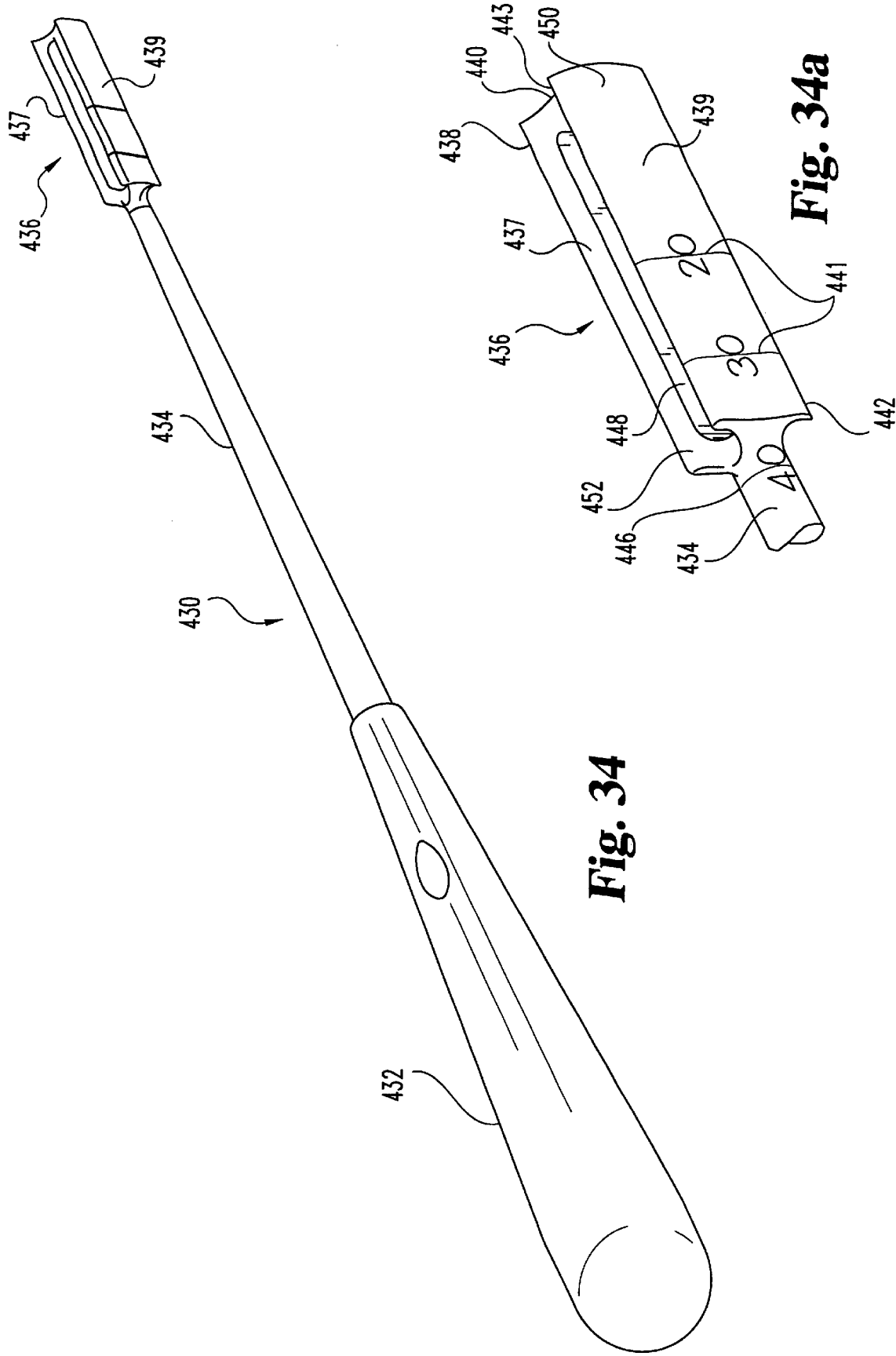

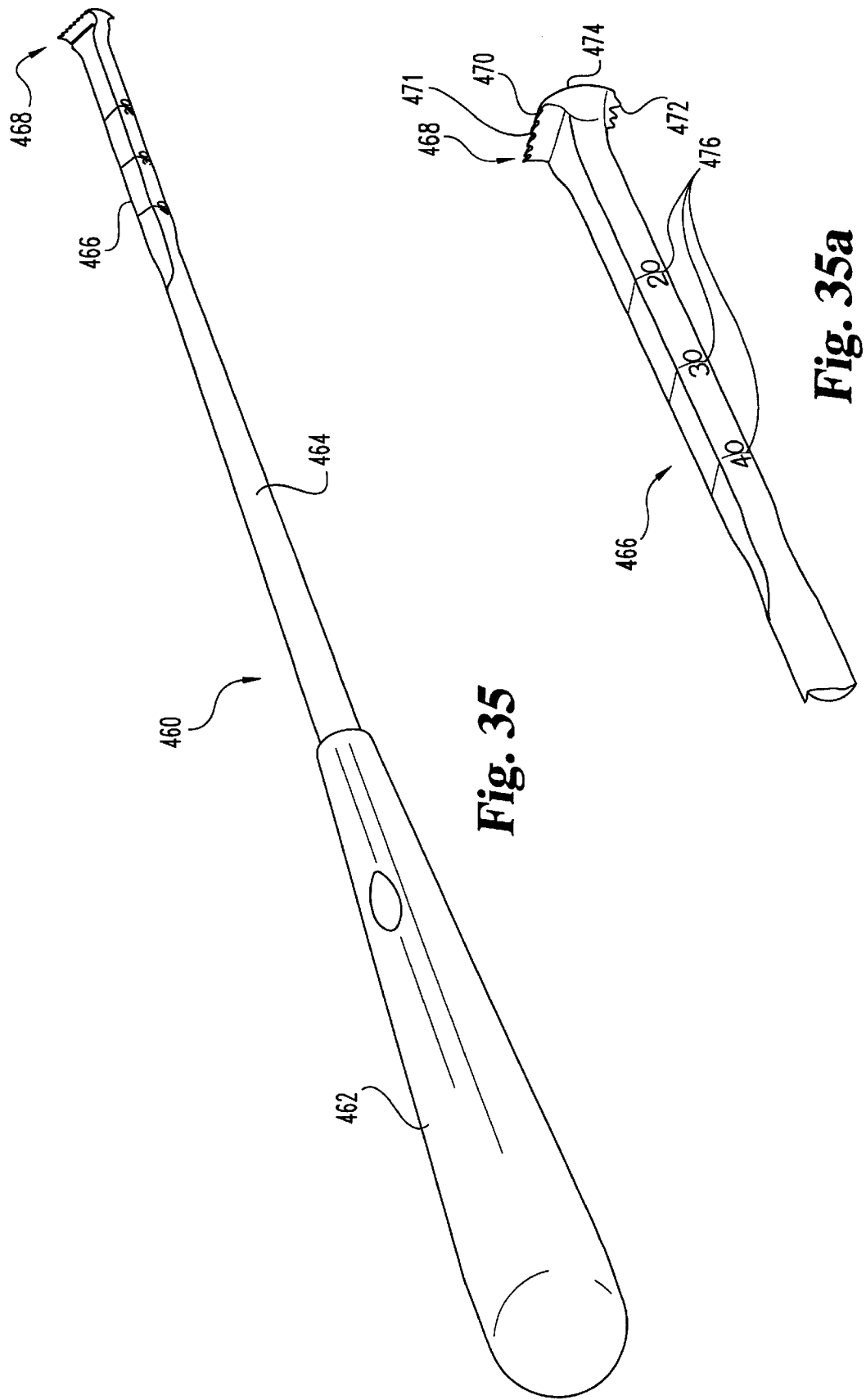

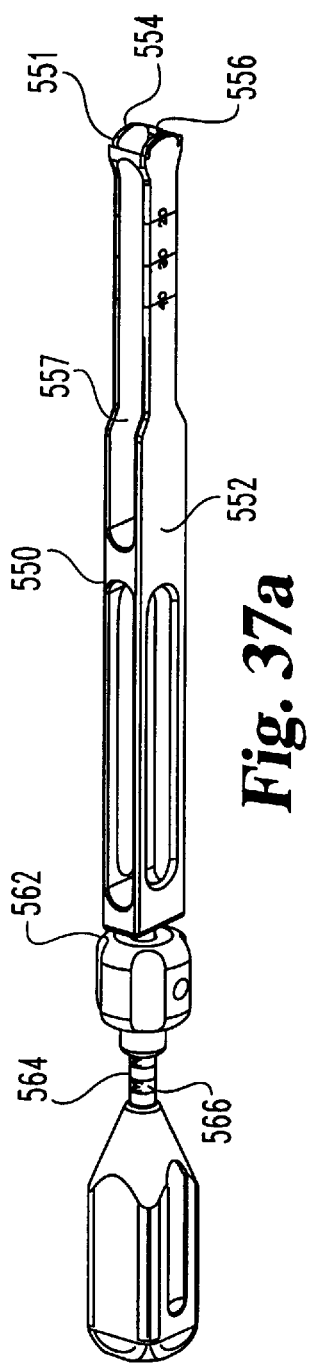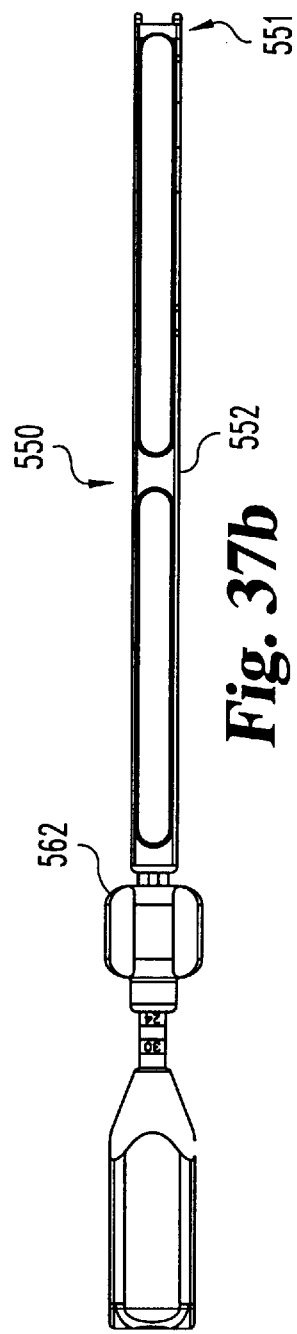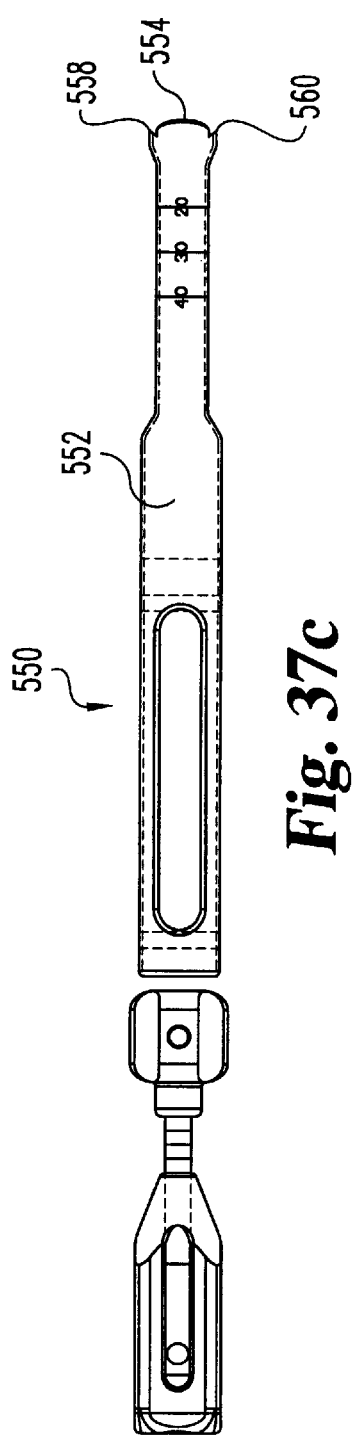

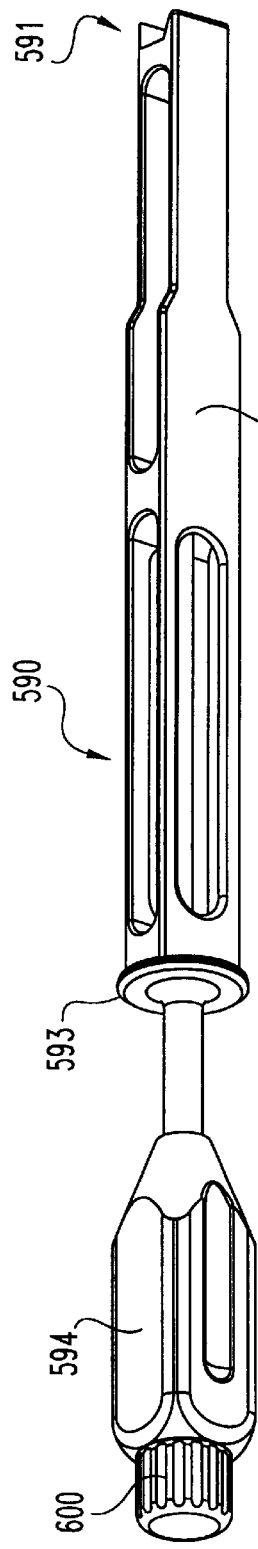
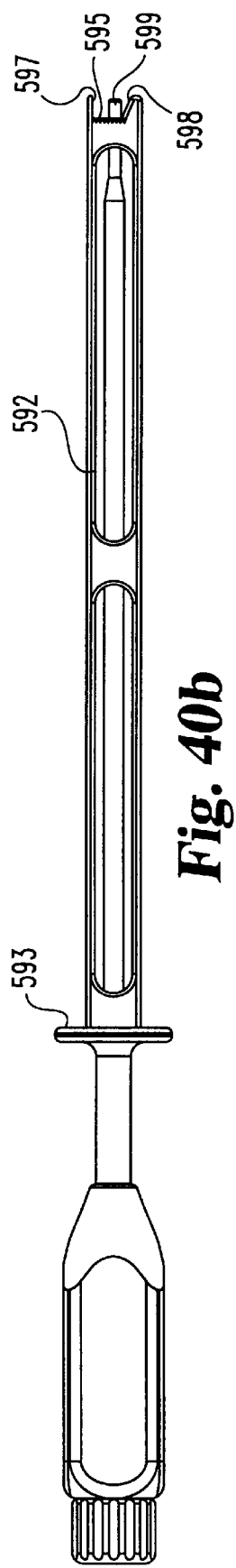
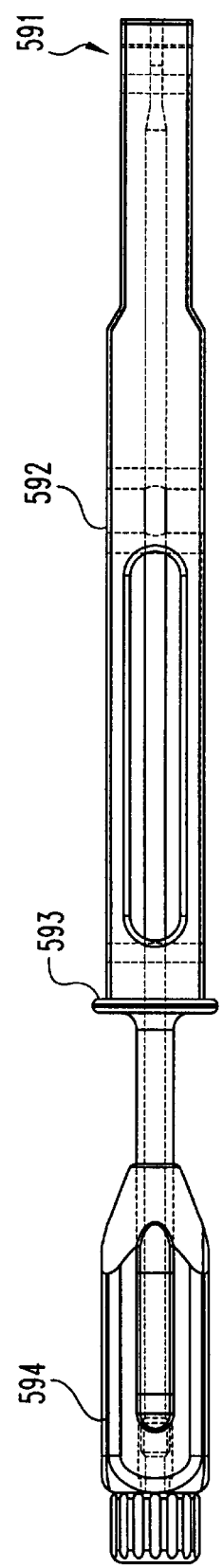
Fig. 40a
Fig. 40b
Fig. 40c

INTERBODY FUSION IMPLANTS AND INSTRUMENTATION

This application is a division of application Ser. No. 09/181,353 filed Oct. 28, 1998, now U.S. Pat. No. 6,174,311.

FIELD OF THE INVENTION

The present invention relates to implants for use in lumbar interbody fusion procedures and instruments for performing such procedure. More specifically, this invention relates to implants formed from donor bone that are useful to restore disc height and promote bone fusion after discectomy and to instruments and methods for preparing the intervertebral space and inserting the implant into an intervertebral space.

BACKGROUND OF THE INVENTION

One of the leading causes of lower back pain and disability results from the rupture or degeneration of one or more lumbar discs in the spine. Pain and instability are caused by compression of the spinal nerve roots because the damaged discs protrude into the vertebral canal and do not provide sufficient biomechanical support for the full range of vertebral motion. Normally intervertebral discs, which are located between endplates of adjacent vertebrae, stabilize the spine and distribute forces between the vertebrae and cushion vertebral bodies. An intervertebral disc includes a semi-gelatinous component—the nucleus pulposus, and a fibrous ring—the annulus fibrosis. The spinal discs may be displaced or damaged due to trauma, disease or aging. A herniated or ruptured annulus fibrosis may result in nerve damage, pain, numbness, muscle weakness, and even paralysis. Furthermore, as a result of the normal aging processes, discs dehydrate and harden, thereby reducing the disc space height and producing instability of the spine and decreased mobility.

Not all patients with damage or spinal deformities require surgical intervention. However, patients who have failed to respond to conservative treatment and who have demonstrable disc pathology often require surgical correction. Most typically the surgical correction includes a discectomy (surgical removal of a portion or all of the intervertebral disc). Discectomy is often followed by fusion of the adjacent vertebrae. To alleviate the pain, abnormal Joint mechanics, premature development of arthritis, and nerve damage, the disc space vacated by the damaged disc must be preserved following discectomy. Therefore, spacers or implants are required between the vertebrae that were adjacent to the resected disc.

Current treatment methods have been unable to accurately control the endplate removal using conventionally designed chisels, scrappers and cutters. Use of conventional surgical instruments does not adequately control the depth of cut into the disc space nor provide a means to accurately the countersink the implant into the prepared cavity-particularly for non threaded impacted. Furthermore, current methodologies do not provide sufficient protection of the neural structures during surgery to prevent neural injury Current treatment methods utilize grafts, either bone or artificial implants, to fill the intervertebral space between adjacent vertebrae. It is desirable that these implants not only fill the disc space vacated by the damaged disc, but also restore the disc space height to pre-damaged condition. An implant must be sufficiently strong to bear substantially all the body's weight above the vertebral space where it is inserted. Furthermore, it is desirable to use the implants to promote fusion of the adjacent vertebrae across the disc space and thereby promote mechanical stability. Current methodologies use implants or spacers made of metal, plastic composites or bone. Use of bone implants offers several advantages over artificial spacers or implants. The bones provide an implant having a suitable modulus of elasticity that is comparable to that of the adjacent vertebrae. The bone implants can be provided with voids, which can be packed with cancellous bone or other osteogenic material to promote bone growth and eventual fusion between adjacent vertebrae. Furthermore, implants formed from cortical bone have sufficient compressive strength to provide a biomechanically sound intervertebral spacer while it is slowly being incorporated or absorbed by the body and substituted for the patient's own bone tissue—colloquially referred to as "creeping substitution."

While it is desirable to use natural bone grafts as implants, use of bone is often limited because of a small supply of suitable sources. Xenografts from non-humans, animals, suffer from rejection problems once implanted. While measures are being taken to limit the human body's rejection of xenografts, greater success is still achieved with bone obtained from human sources. The best source is an autograft from the patient receiving the graft. Removal of an autograft requires further surgery and is limited in amount and structural integrity by the patient's anatomy. The alternative source of human bone grafts is allografts harvested from human donors. Since the number of people donating tissue to science is small, these bone grafts represent an extremely valuable and rare commodity. Current methodologies for providing cortical bone implant spacers typically require cutting the spacer, usually in the form of a dowel, from the diaphysis of a long bone. Only a certain portion of the diaphysis is sufficiently thick to provide dowels with requisite strength to maintain the intervertebral space. For example, in a human femur only about the middle third of the diaphysis, where the shaft is narrowest and the medullary canal is well formed, has sufficient bone wall thickness and density to be used to prepare cortical dowels. The suitable portions of the diaphysis are sliced, and then a plug is cut from each slice. The plugs are then machined to form a dowel. Most often the dowel includes the medullary canal to provide a depot for osteogenic material and promote fusion of the adjacent vertebrae. Much of the donor bone is wasted, particularly the remnants of the slices from the diaphysis used to provide the dowels as well as the end portions of the long bone which cannot be utilized. Above and below this middle section of the diaphysis, the walls of the femur bone become thinner because of the separation of the layers of the bone into cancelli. Thus, these portions of the femur are not considered suitable for forming cortical dowels having the required dimensions for inserting into vertebral spaces. Use of these remnants would provide a more efficient use and conservation of a limited and very valuable natural resource of cortical bone.

Thus, there remains a need for improved bone graft implants and instruments for their placement in the body.

SUMMARY OF THE INVENTION

Thus, there is provided with the present invention an implant prepared from bone. The implant has a shaped body and sufficient length to extend from an anterior portion of a vertebral body to a posterior portion and a height sufficient to separate adjacent vertebrae. The implant comprises a bone portion having an upper and lower bone engaging surface, a first sidewall and an opposite second sidewall. The first and second sidewalls extend between the upper and lower bone engaging surfaces. Furthermore, the first sidewall includes a portion defined by a concave surface. Preferably, the implant also includes a recessed region that serves as a depot or receptacle for deposition of osteogenic material to enhance bone growth and eventual fusion of the adjacent vertebrae. One end of the implant is provided with structural features to engage an implant holder; in a preferred embodiment, the other end of the implant is provided with a shape to ease insertion into the intervertebral space. The implant prepared according to the present invention has sufficient biomechanical support to maintain the desired intervertebral space while it is gradually being replaced with new bone growth. In specific embodiments of the present invention, the implant is provided in the form of a J-shape; in other specific embodiments the implant is provided in the form of a crescent shape.

There is also provided in accordance with the present invention an implant holder. The implant holder includes a gripping head for releasably securing the implant. Preferably the impact holder also includes an impacting surface for driving the implant into a preformed cavity in the intervertebral space. The gripping head includes at least one implant engaging structural feature, such as a pin. Optimally, the pin includes at least a radiopaque portion to provide a means for viewing placement of the implant via radiography during surgery. In one embodiment, the gripping head on the implant includes a surface preferably roughened or knurled to secure the implant into the preformed cavity. In another embodiment of the present invention, the implant holder including the gripping head includes at least two surfaces. Each of the surfaces includes a pin that releasably secures the implant to the gripping head by matingly engaging recesses in the implant. The implant holder of the present invention securely holds the implant so that it can be impacted into the preformed cavity in the intervertebral space and then releases the implant so it remains in the cavity.

There is also provided in the present invention instruments for preparing an intervertebral space for receiving the final fusion implant. The instruments include a chisel for preparing the intervertebral space to receive the implant, preferably by cutting a cavity in the opposing endplates of adjacent vertebrae. The bone chisel includes at least two cutting edges. The bone chisel also includes opposing curved surfaces extending distally beyond the cutting surface to center the chisel and the cutting edges between the opposing surfaces of adjacent vertebrae. When the chisel and cutting blades are centered between the opposing surfaces, the blades cut equally from both surfaces.

Other instruments included for use in the present invention include scrapers, rotating scrapers, and impacting or "slap" hammers for driving the implants into position. The slap hammer allows for controlled impacting force and removal of the chisel after cutting.

Another aspect of the present invention includes a nerve retractor blade assembly for manipulation of neural structures such as the dural sac and traversing nerve root with minimal trauma to the respective structures. The assembly includes a retractor having a channel adapted to receive a retractor blade, a retractor blade and can include at least one pin, preferably two pins, for securely fixing the positioning of the retractor assembly and blade proximal to the intervertebral space. The blade can be adapted for engagement with the retractor and for extending into the intervertebral space to provide anchorage proximal to the disc space, maintain disc height and maintain distraction. The nerve retractor also includes a handle attached at an angle to the channel. In a preferred embodiment, the retractor channel is provided in the form of a concave channel. It is also contemplated that the retractor channel can be formed in a variety of other shapes, for instance, rectangular and broadened V-shaped channels are also included within the present invention.

Yet another aspect of the present invention includes a protective guide sleeve. The protective sleeve includes a body having a hollow core for receiving instruments for performing surgery. In addition, the protective sleeve provides a narrow but unobstructed passageway to the intervertebral space and minimizes the area of tissue impacted by the surgery. Preferably the protective sleeve includes a first and a second distractor fin that can be inserted into the intervertebral space to maintain the space height and alignment of the vertebrae. The protective sleeve provides protection for neural structures and prevents encroachment of the neural structures into the surgical area. The protective sleeve allows use of depth stop on surgical tools. Preferably, the protective sleeve includes at least one window to facilitate visualization. The instruments for preparing and inserting spinal fusion implants can be received within the protective sleeve. Such instruments include the implant holder engaged to an implant, the bone chisel, scrapers, and drills provided in the present invention.

Accordingly, it is one object of the present invention to provide an improved implant of bone to maintain an intervertebral space after discectomy.

It is another object of the present invention to provide an implant holder to releasably secure the implant and facilitate impaction of the implant into position within the intervertebral space.

It is still another object of the present invention to provide a cutting chisel to prepare a cavity in the intervertebral space between two opposing adjacent endplates on vertebrae.

It is yet another object of the present invention to provide a retractor for manipulation of neural structures.

Further objects, features, benefits, aspects and advantages of the present invention shall become apparent from the detailed drawings and descriptions provided herein.

BRIEF DESCRIPTION OF THE DRAWINGS

FIG. 1 is a perspective view of one embodiment of an implant according to the present invention.

FIG. 2 is a side view of the implant of FIG. 1.

FIG. 2a is an enlarged view of a portion of the side of the implant of FIG.2 illustrating the ridges for engaging bone.

FIG. 3 is a top elevated view of the spacer of FIG. 1.

FIG. 4 is an end view of the tool engaging end of the implant of FIG. 1.

FIG. 5 is a side sectional view of an implant revealing the tool receiving slots and recesses.

FIG. 6 is an end view of the insertion end of implant of FIG. 1.

FIG. 7 is an elevated top view of one embodiment of an implant holder according to the present invention.

FIG. 8 is an end view of the implant holder of FIG. 7.

FIG. 9 is a side view of the implant holder of FIG. 7.

FIG. 10 is a perspective view of the holder of FIG. 7.

FIG. 13 is side view of the implant of FIG. 12.

FIG. 14 is an elevated top view of the implant of FIG. 12.

FIG. 15 is an end view illustrating the tool attachment end of the implant of FIG. 12.

FIG. 16 is an end view illustrating the insertion end of the implant of FIG. 12.

FIG. 17 is an elevated top view of an alternative embodiment of an implant holder according to the present invention for use with the implant of FIG. 12.

FIG. 17a is an enlarged view of a gripping head of the implant holder of FIG. 17.

FIG. 18 is a side view of the implant holder of FIG. 17.

FIG. 18a is an enlarged top view of the gripping head of implant holder of FIG. 17.

FIG. 18b is a first end view of the implant holder of FIG. 17.

FIG. 19 is a side view of the implant of FIG. 12 engaged in the implant holder of FIG. 17.

FIG. 20a is an elevated top view of the implant of FIG. 12 engaged in the implant holder of FIG. 17.

FIG. 20b is a first end view of the implant of FIG. 12 engaged in an implant holder of FIG. 17.

FIG. 21 is a perspective view of an implant of FIG. 12 engaged in an implant holder of FIG. 17.

FIG. 26 is a perspective view of a bone shaver according to the present invention.

FIG. 26a is a perspective view of the cutting head of the bone shaver of FIG. 26.

FIG. 30 is a perspective view of the retractor blade for the retractor of FIG. 29.

FIG. 30a is a partial perspective view of the lead tip of retractor blade in FIG. to 30.

FIG. 32 is a perspective view of a round scraper for use in the present invention.

FIG. 32a is a partial perspective view of the scraper head of the round scraper depicted in FIG. 32.

FIG. 32b is a side view of the round scraper of FIG. 32.

FIG. 32c is an elevated top view of the round scraper of FIG. 32.

FIG. 32d is a partial perspective view of the scraper head of the round scraper of FIG. 32.

FIG. 32e is an elevated top view of the scraper head of the round scraper of FIG. 32. FIG. 32.

FIG. 32f is a side view of the scraper head of the round scraper of FIG. 32.

FIG. 33 is a perspective view of a plane scraper for use in the present invention.

FIG. 33a is a partial perspective view of the scraper head of the plane scraper depicted in FIG. 33.

FIG. 33b is a side view of the plane scraper of FIG. 33.

FIG. 33c is an elevated top viewof the plane scraper of FIG. 33.

FIG. 34 is a perspective view of a rotatable cutter for use with the present invention.

FIG. 34a is a partial perspective view of the cutting head of the rotatable cutter depicted in FIG. 34.

FIG. 35 is a perspective view of a toothed scraper for use according to the present invention.

FIG. 35a is a partial perspective view of the cutting head of the toothed scraper depicted in FIG. 35.

FIG. 37a is a perspective view of an alternative embodiment of a chisel for use in the present invention.

FIG. 37b is an elevated top view of the chisel in FIG. 37a.

FIG. 37c is a side view of the chisel in FIG. 37a.

FIG. 39b is an elevated top view of the implant folder depicted in FIG. 39a.

FIG. 39c is a side view of the implant holder depicted in FIG. 39a.

FIG. 39d is a cross-sectional view of the implant depicted in FIG. 39a.

FIG. 39e is an enlarged view of the gripping head of the implant depicted in FIG. 39a.

FIG. 39f is a perspective end view of the gripping head of the implant depicted in FIG. 39a.

FIG. 40a is a perspective view of an implant inserter according to the present invention.

FIG. 40b is an elevated top view of the implant inserter depicted in FIG. 40A.

FIG. 40c is a side view of the implant inserter depicted in FIG. 40A.

FIG. 44c is a perspective view of a cortical bone dowel formed from the diaphysis section of 44a.

DETAILED DESCRIPTION OF THE PREFERRED EMBODIMENTS

Figure 11:
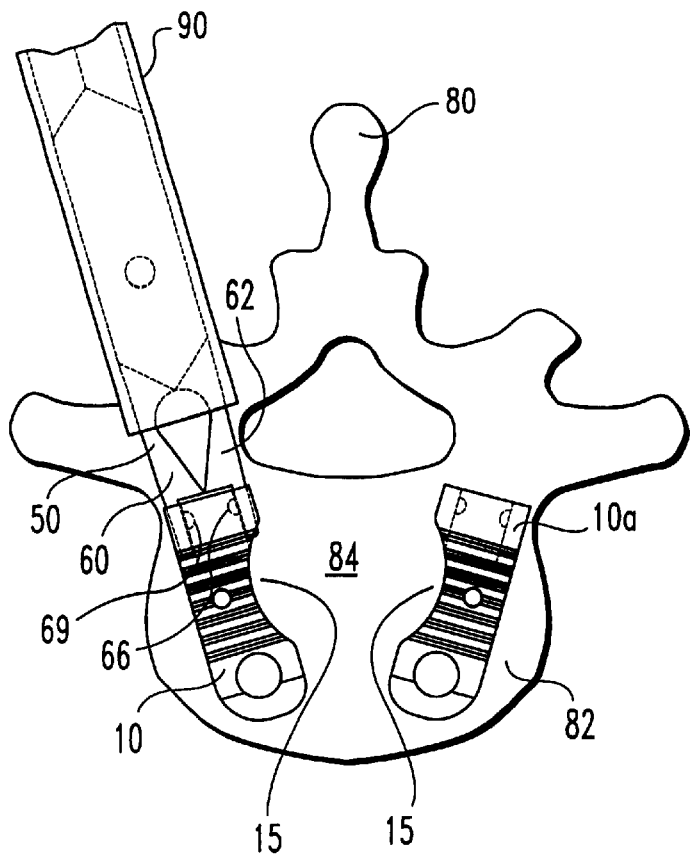
FIG. 11 is a cutaway view of an intervertebral space that includes an implant seated within the intervertebral space and seating a second implant using the implant holder of FIG. 7.
Figure 12:
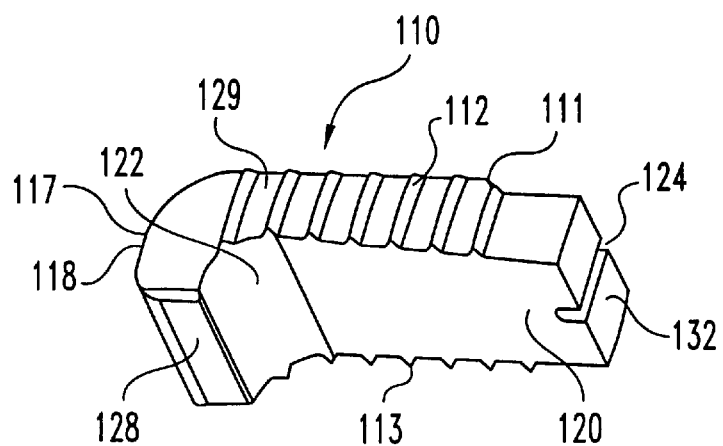
FIG. 12 is a perspective view of an alternative embodiment of a J-shaped implant according to the present invention.

For the purposes of promoting an understanding of the principles of the present invention, reference will now be made to the embodiments illustrated in the drawings, and specific language will be used to describe the same. It will nevertheless be understood that no limitation of the scope of the invention is intended thereby. Any alterations and further modification in the described processes, systems, or devices, and any further applications of the principles of the invention as described herein are contemplated as would normally occur to one skilled in the art to which the invention relates.

This invention provides bone implants for insertion into the intervertebral spaces between adjacent vertebrae following discectomy. The bone implants are useful for maintaining and/or restoring a desired spacing between adjacent vertebrae. The bone implants of the present invention include a recessed area that serves as a depot for receiving osteogenic material, thereby enhancing bone ingrowth and fusion of the adjacent vertebrae. The implants of the present invention are designed to conserve donor bone material without compromising necessary biomechanical properties of the implant to support the forces generated at the implantation level. Multiple implants according to the present invention may be formed from a single donor bone. Further, the implants according to the present invention may be obtained from remnants of donor bone utilized to form alternative implants and from the upper and lower end portions of the diaphysis of long bones lacking the required properties for cylindrical dowels, collectively referred to herein as "remnants." Preferably, each implant includes at least a portion influenced by the shape of the medullary canal. Preferably, the medullary canal is included as a curved surface in the body of the implant that can serve as a depot for osteogenic material. Optimally, the design of the implant includes surface features which inhibit expulsion of the implant from the preformed cavity.

Referring now to FIG. 1 through FIG. 6, one embodiment of an implant according to the present invention is illustrated. Implant 10 includes body 11 having a concave surface 14 that defines a recessed area 15 into body 11. Implant 10 further includes a tool attachment end 32 adapted for engagement with an implant holder. Tool attachment end 32 can include a variety of recesses, receptacles, grooves, slots, projections, and other supporting members to engage corresponding surface features on an implant holder. Implant 10 also includes an insertion end 17. On the implant illustrated in FIGS. 1–6, the insertion end is defined by curved surface 18. It is understood that curved surface 18 can also include surfaces having a uniform and non-uniform curvature and tapered ends for increasing the ease of insertion of the implant into the intervertebral space.

Body 11 of implant 10 is substantially elongated and defines a longitudinal axis 19. The length of the implant 11 is sufficient to provide sufficient support and stability to the spinal column. Typically the implant has a length of about 21 mm to about 27 mm, more preferably, about 22 to about 26 mm. When viewed from the side, the height of implant 10 can be substantially uniform for its entire length, which lies parallel to the longitudinal axis. Alternatively, as illustrated in FIG. 2, the height of implant 10 can vary along its length. The maximum height of implant 10 is about 11 mm to about 15 mm in height as shown by reference line 21. The lesser height 23 of implant 10 is about 7 mm to about 11 mm. The maximum width 25 of implant 10 may not exceed the width of the bone remnants, which serve as the source of donor bone for the implants. However, the implant is formed with a sufficient maximum width to adequately support the forces generated at the site of implantation and to provide stability to the implant to inhibit rotation in the disc space. Furthermore, in preferred embodiments, the width of the implant is sufficient to withstand a downward applied compressional force of about 30,000 Newtons. The width of the implant is about 8 mm. to about 14 mm, more preferably about 10 mm to about 12 mm.

The outer surface of implant 10 can include surface features such as ridges or teeth to prevent retropulsion of the implant from the intervertebral space. Ridges 12 can be randomly or uniformly distributed about the outer surface of implant 10. The ridges 12 can be distributed on one, two, three, or four sides of the exterior surface of implant 10. Preferably, ridges 12 and 13 are located on the upper surface 40 and lower surface 42, respectively. Ridges 12 and 13 are defined as an equilateral triangle defining an angle of about 50 to about 70° at the apex and having a height of about 1 mm.

Body 11 of implant 10 includes a recessed area 15 that can be used for receiving osteogenic material. One side of implant 10 includes concave surface 14 formed as a result of the medullary canal of the long bone. While concave surface 14 generally follows the contours of the medullary canal of the donor bone, it will be understood that cleaning and preparing the bone graft from the donor may slightly alter the medullary canal, thereby altering the configuration of concave surface 14. Moreover, concave surface 14 typically resembles a portion of a cylindrical wall. However, the specific configuration of the surface may vary, depending on the shape of the medullary canal in the donor bone. Concave surface 14 defines a recessed area 15. In addition to concave surface 14, the implant can include other apertures such as apertures 20 and 22. In preferred embodiments, apertures 20 and 22 extend through implant 10 and are sized to receive a sufficient amount of an osteogenic material to promote bone ingrowth and fusion of the adjacent vertebrae.

Implant body 11 includes a substantially flat side 16 opposite concave surface 14. Flat side 16 adjoins tool engagement end 32 and extends along the length of body 11 to abut insertion end 17. It is understood for the purposes of this invention that flat side 16 is substantially planer. However, it is also within the scope of the present invention that flat side 16 can include a curved surface, if desired.

Tool attachment end 32 can include a variety of recesses, apertures, and other structural features to engage an implant holder. For example, as depicted in FIGS. 4 and 5, tool engagement end can include slots 24, 26, first indent 28 and second indent 30. First indent 28 and second indent 30 can be provided to matingly engage corresponding pins on an implant holder.

Insertion end 17, which includes rounded surface 18 is depicted in FIG. 6. It is desirable, but not necessary, that rounded end 18 defines a uniform curvature as depicted in FIG. 6. It is desirable to round over or streamline the end of implant body 10 to ease the insertion of the implant into a preformed cavity. Therefore, in addition to curved surface 18, the implant also includes incline surfaces 34 and 36. Inclined surfaces 34, 36 and curved surfaces 18 may be provided to facilitate insertion of the implant into the preformed cavity. As explained further herein, such curved end surfaces obviate the necessity to provide a squaring off of the bottom of the channel of the preformed cavity.

It is also provided with the present invention an implant holder for releaseably securing and impacting the implant of FIGS. 1–6 into the preformed cavity. One embodiment of the implant holder is depicted in FIGS. 7–10. Implant holder 50 includes handle 70, gripping head 59, first branch 52 engaged to handle 70 and second branch 54. Second branch 54 is pivotally attached to first branch 52 with pivot pin 56. Gripping head 59 includes a first gripping arm 60 integral to second branch 54 and a second gripping arm 62 integral to first branch 52. Thus, in preferred embodiments gripping arm 62 remains stationary while gripping arm 60 pivots on pivot pin 56 to provide access to a recess cavity 68 formed between opposing gripping arms 60 and 62. Gripping arms 60 and 62 include projections 64 and 66, respectively. Projections 64 and 66 are adapted to matingly engage first indent 28 and second indent 30 on implant 10. Furthermore, gripping head includes a surface for contacting the tool engaging end 32 of implant 10 to drive the implant into a preformed cavity. In the preferred embodiment illustrated in FIGS. 7–10, gripping arms 60 and 62 include impacting surfaces 61 and 63, respectively. Impacting surface 61 abuts and is substantially orthogonal to the interior side of gripping arm 60. Impacting surface 63 is similarly disposed on gripping arm 62.

Opposite end of gripping arms 60 and 62 are first branch 52 and a second branch 54, respectively. First branch 52 is connected to handle 70 and remains stationary along with gripping arm 62. However, second branch 54 on the opposite end of gripping arm 60 opens by pivoting on pivot pin 56.

Pivoting of branch 54 on pivot pin 56 causes gripping arm 60 to move away from gripping arm 62 and, thus, open the recessed cavity 68 to receive tool engaging end 32 of implant 10. After receiving tool engaging end 39, second branch 54 is then pivoted towards first branch 52 to close recess cavity 68 and securely engage the projection 64 and 66 into first and second attachment recesses 24 and 26 and first and second indents 28 and 30 on implant 10.

Once branching arm 54 abuts or nearly abuts branching arm 52, locking pin 58 engages first branch 52 and prevents pivoting of second branch 54. Implant 10 can be released from implant holder 50 by disengaging locking pin 58 and pivotally opening second branch 54 from first branch 52. Alternatively, other locking means such as a slidable sleeve or a collect that are adapted to encircle first and second branches and prevent opening of the gripping arms can be used with the present invention. While locking pin 58 is illustrated in FIGS. 8–10 as one embodiment of securely engaging implant 10, it is contemplated that other locking means or mechanisms known to those skilled in the art can be used with the present invention.

Implant holder 50 engaged to implant 10 can be used to insert the implant into the intervertebral space as depicted in FIG. 11. Insertion tube 90 is inserted into disc space 82 in a far lateral PLIF approach that can be used with a transforminal procedure. Implant 10a is depicted as fully seated in a first preformed cavity adjacent to vertebral body 80. In a preferred embodiment, insertion tube 90 is first positioned adjacent the preformed cavity. Insertion tube 90 is adapted to slidably receive implant 10 and implant holder 50. After implant 10 is securely engaged in the preformed cavity, locking pin 58 is released, thereby allowing second branch 54 to pivot away from first branch 52 and release engagement of projections 64, 66, and gripping arms 60 and 62 from the corresponding attachment recesses and indents on implant 10. Insertion tube 90 may be sized to permit movement of the branches therein or may be withdrawn to allow sufficient movement for disengagement. Implant holder 50 and insertion tube 90 are then removed.

Figure 11A:
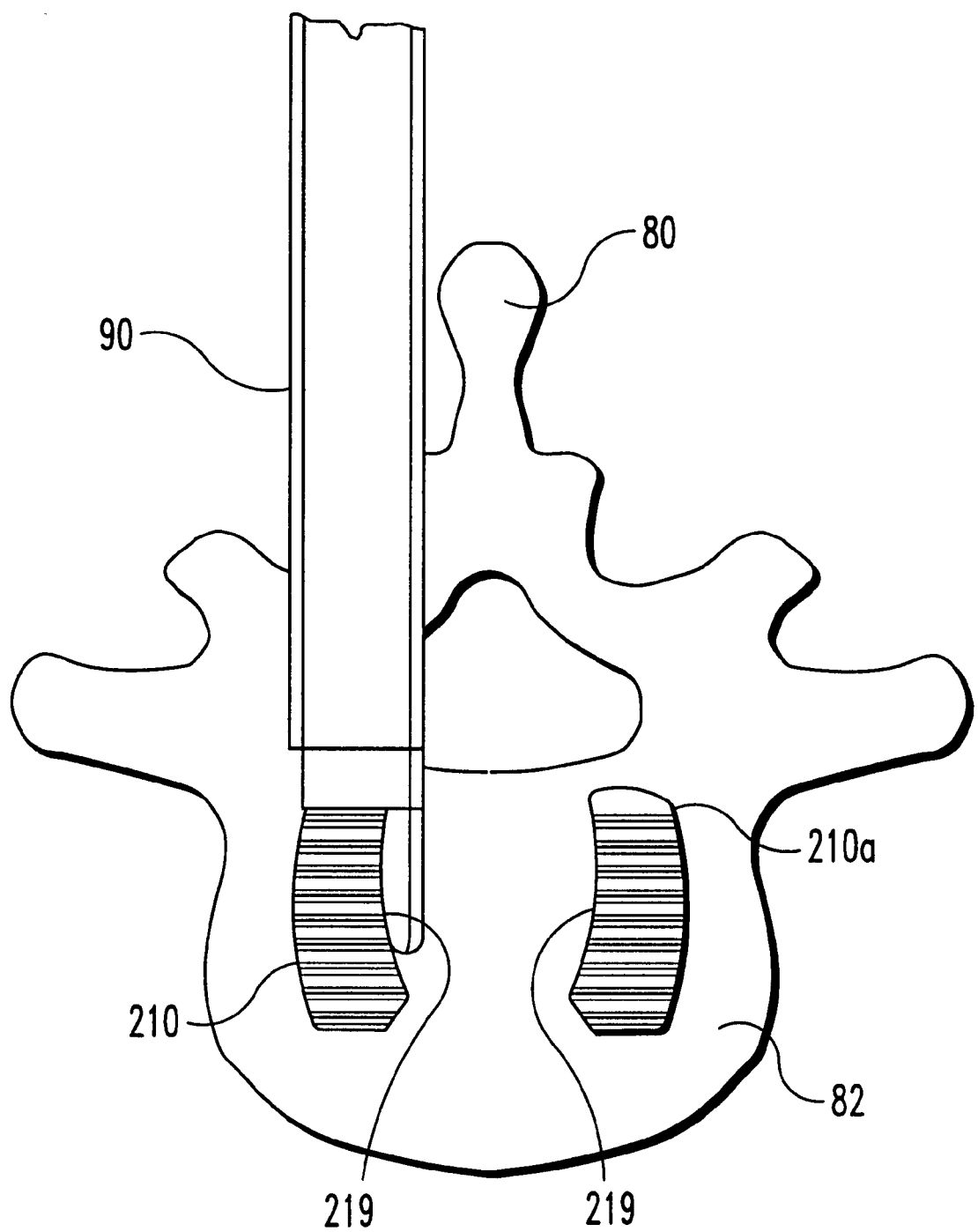
FIG. 11a is a cutaway view of an intervertebral space that includes an crescent shaped implant seated within the intervertebral space and seating a second implant using an implant holder.

In FIG. 11a a crescent implant and an implant holder disposed within the disc space is illustrated. A first implant 210a is depicted as fully seated in the disc space 82. Insertion tube 90 provides access to the disc space 82 from the posterior side of the vertebral body 80 for insertion insertion of implant 210. Recessed areas 219 on implants 210 and 210a are disposed medially.

An alternative embodiment of an implant prepared according to the present invention is depicted in FIGS. 12–16. Implant 110 is formed in elongated J-shaped body 111 that defines a longitudinal axis 119. One side of J-shaped body 111 includes curved section 122 that adjoins J-end 128 to form the crook of the J-shape and is bounded by straight section 120 opposite J-end 128. In a preferred embodiment, curved section 122 includes internal concave surface 114. Preferably, concave surface 114 is contoured based on the medullary canal of a long bone. Straight section 120 abuts tool attachment end 132. Tool attachment end 132 includes tool engagement recess 124 for securely engaging an implant holder. Tool engagement recess 124 is adapted to secure implant 110 in the implant holder to minimize vertical movement of the implant while the implant is being inserted into preformed cavity. It is contemplated that the tool engagement end 132 can further include a variety of tool engagement structures, such as grooves, receptacles, holes, recesses, projections, pins, and detents. Upper tool recess 126 is disposed between tool engagement end 132 and flat side 116. Flat side 116, which is opposite straight section 120, defines the back or laterally disposed portion of J-shaped body 111 and abuts insertion end 117 on one end and on the opposite end abuts shoulder 127. Insertion end 117 includes curved surface 118. While not specifically illustrated in FIGS. 12–16, implant 11 is provided to have a length, height and width as described for implant 10.

A plurality of ridges 112 and 113 are provided on the top surface 129 and bottom surface 130 of implant 110. It is more or less depicted that top surface 129 and bottom surface 130 include a series of ridges 112 and 113. However, it is contemplated that ridges can be defined on one, two, three or four sides of implant 110.

An alternative preferred embodiment of an implant holder is illustrated in FIGS. 17–21. Implant holder 150 includes a shaft 151 that defines a longitudinal axis 164. The shaft 151 includes gripping head 152 on one end and coupling point 153 on the opposite end. The shaft splits into an upper branch 154 and a lower branch 156. The upper and lower branches are separated by channel 158. Upper branch 154 includes upper branch extension 160, and lower branch 156 includes lower branch extension 170. Collectively upper branch extension and lower branch extension define the gripping head 152.

The gripping head 152 includes at least one implant engaging structure. Preferably gripping head includes projections 166 and 168 that engage in corresponding recesses in the implant. The projections are provided to control lateral and vertical motion as the implant is impacted into the intervertebral space. Optimally, gripping head also includes a surface that can be used to impact or drive the implant in the preformed cavity.

In preferred embodiments, the gripping head illustrated in FIGS. 17–21 includes upper and lower branch extensions 160 and 170, respectively. Upper branch extension 160 includes incline surface 162, which is provided to matingly engage straight section 120 on implant 110. Branch extension 160 includes tapered end 166 that matingly engaging tool engagement recess 124. Lower branch extension 170 includes end 172 for engaging shoulder 127 on implant 110. Furthermore, lower branch extension 170 includes tapered end 168, which along with tapered end 166, is provided for engaging tool engagement recess 124. Tapered ends 166 and 168 engage in tool recess 124 to prevent lateral movement of the implant during impacting to force the implant into the preformed cavity.

As shown in FIG. 19, the shaft also includes outer sleeve 184, which is moveable along the shaft in a direction parallel to the longitudinal axis and urges the upper and lower branches together when the outer sleeve 184 is moved in the direction toward gripping head 152. Movement of outer sleeve 184 is controlled by the threaded engagement of threaded nut 182 with external threads 157. Outer sleeve 184 includes an internal surface (not shown) adapted to engage inclined surfaces 155 and 159 on the inner shaft to urge the branches together.

Moving outer sleeve 184 on shaft 151 toward the gripping head urges upper and lower branches 154 and 156 and upper and lower branch extensions 160 and 170 toward each other. Thus, upper and lower branches clamp and secure an implant in the gripping head.

Coupling point 153 is included on shaft 151 opposite from gripping head 152. Coupling point 153 is used to attach a handle 180 or an impacting tool to drive an included implant in to preformed cavity.

In FIGS. 19–21, implant 110 is depicted mounted in implant holder 150. Upper and lower branch extensions 160 and 170 clamp implant in gripping head 152. FIG. 20a and 21 illustrate the implant engaged in an implant holder. The implant and holder are superimposed on top of an idealized outline of the superior surface of a lumbar vertebra body. The implant is positioned to lie inside the lateral edges of the vertebral body. The concave area is positioned to face medially. A second implant may be positioned on the opposite side of the vertebral body. The concave areas of the two implants would face each other to form a enclosed area to serve as a depot for osteogenic material.

Figure 22:
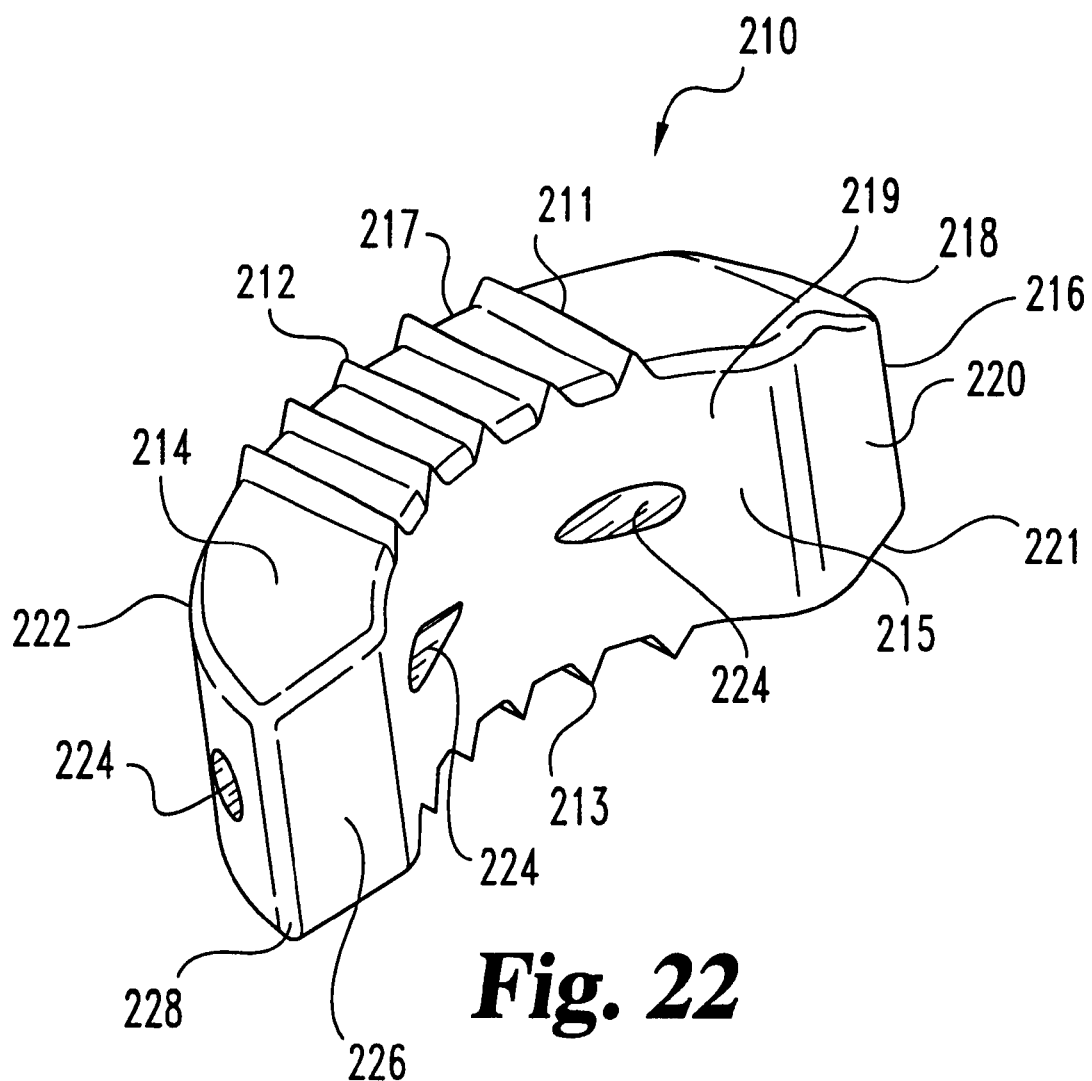
FIG. 22 is a perspective view of another alternative embodiment of a crescent-shaped implant according to the present invention.

Yet another embodiment of an implant according to the present invention is depicted in FIG. 22. Implant 210 includes crescent-shaped body 211 having a convex surface 217 and an opposite concave surface 215. Convex surface 217 is disposed between tool-engaging end 222 and opposite insertion end 216. Implant 210 is depicted as having a series of ridges 212 projecting out of upper surface 214 and similar ridges 213 projecting from the lower surface for engaging bone surfaces. It is understood that implant 210 can be prepared having a fewer number of ridges than depicted in FIG. 22. For example, implant 210 can include surfaces having no ridges, or ridges on one, two, three, or four or more surfaces. Implant 210 is provided with a length, height and width as is generally described for implant 10.

Concave surface 215 adjoins abutting surface wall 226 and on opposite end adjoins taper surface 220. While concave surface 215 gradually follows the contours of the medullary canal, it is understood that cleaning and machining the bone graft from a donor may slightly alter the medullary canal, thereby altering the configuration of concave surface 215. Preferably, a portion of concave surface 215 is formed from a section of the medullary canal of a long bone. Concave surface 215 defines a recessed area 219 that serves as a depot for osteogenic material.

Insertion end 216 is provided to increase the ease of insertion of the implant into a preformed cavity. Thus, it is within the scope of this invention to provide insertion end 216 having a substantially streamlined shape. For example, insertion end 216 can include a bullet-shape, a curved shape, a frustoconical shape and/or a conical shape. In the preferred embodiment illustrated in FIG. 22, insertion end 216 is bounded on three sides by tapered surfaces 218, 220 and 221. While not specifically illustrated in FIG. 22, insertion end 216 also can be bounded by a fourth tapered surface opposite tapered surface 220. Alternatively, opposite tapered surface 220, insertion end 216 can abut convex surface 217.

Tool engaging end 222 is opposite of insertion end 216 on crescent shaped body 211. As with other preferred embodiments of the implants for use with the present invention, tool engaging end can include a variety of recesses, receptacles, grooves, slots, projections, and other supporting members to engage corresponding surface features on an implant holder. In the preferred embodiment illustrated in FIG. 22, tool engaging end 222 includes central opening 224. Central opening 224 is provided for slidably receiving a pin or a rod extension on an implant holder. Preferably central opening 224 is provided with internal threads for threadedly engaging a threaded pin or rod extension on an implant holder. Central opening 224 can extend over about 50% through body 211, more preferably central opening extends greater than about 80% through body 211. Most preferably, central opening 224 extends through body 211 of implant 210 so that an inserted pin or rod extension extends through or to insertion surface 216. In preferred embodiments, central opening 224 contains a uniform cross-sectional area throughout. It is understood that central opening 224 can include segments with different diameters and/or taper from tool engaging end to insertion end 216 to receive a pin or rod extension of an implant holder that has the corresponding segment(s) or taper. (See, for example, the rod extension 246 in FIG. 32a). It is depicted in FIG. 22 that central openina 224 extends through the recessed area 219 defined by concave surface 215; however, it is understood that alternative embodiments of implant 210 may provide a central opening 224 that extends through or part way through implant 210 without accessing the recessed area 219.

Figure 23:
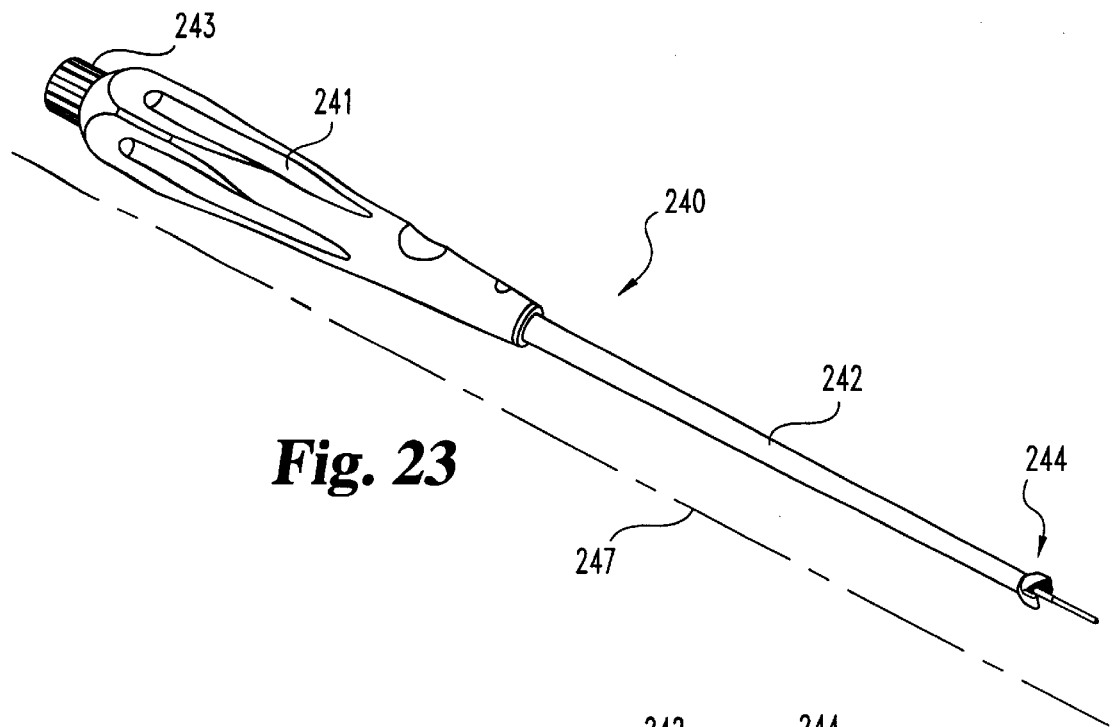
FIG. 23 is a perspective view of another alternative embodiment of an implant holder according to the present invention.
Figure 23A:
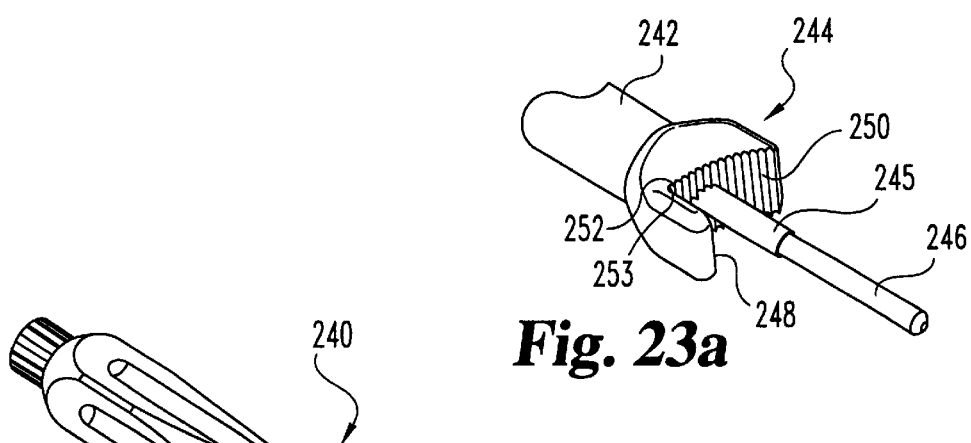
FIG. 23a is an enlarged perspective view of the gripping head of the implant holder of FIG. 23.
Figure 24:
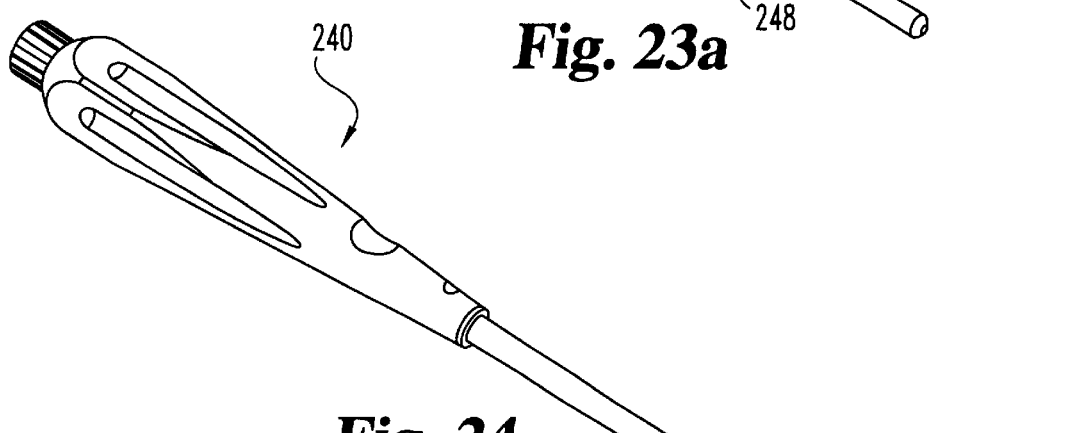
FIG. 24 is a perspective view of the implant of FIG. 22 engaged in the implant holder of FIG. 23.

Yet another embodiment of an implant holder is depicted in FIGS. 23–24. Implant holder 240 includes extension 243, handle 241, shaft 942, and gripping head 244. Shaft 242 defines a longitudinal axis 247. Gripping head 244 includes a first surface 250 for abutting and impacting the tool engaging end 222 to drive implant 210 into a prepared cavity. Thus, the implant holder not only releaseably secures an implant, but also provides a means for impacting the implant into a preformed cavity. Preferably, first surface 250 is roughened to better secure engaged implant 210. Gripping head 244 also includes a holder extension 248 adjoining first surface 250 at comer 252 at an included angle 253 of about 90°, preferably orthogonal to the direction of impaction or insertion. However, in alternative embodiments, holder extension 248 can abut the first surface 250 and form an included obtuse angle 953 between the first surface and the holder extension. Alternatively, the holder extension 248 can abut the first surface 250 and form an acute included anale 953 between the first surface and the holder extension. (See, for example, similar structure inclined surface 162 in FIG. 17a). It is understood that the angle between the first surface and holder extension 248 can be provided to frictional secure abutting surface 226 and tool engagino end 292 on implant 210. Thus, holder extension 248 can be adapted to inhibit lateral movement of the implant as it is impacted in the cavity.

Gripping head 244 also includes first rod extension 246. First Rod extension 246 can include external threads for engaging internal threads in a tool receiving recess in an implant. Preferably rod extension 246 is radiopaque to provide an X-ray indicator of the location of the implant during surgery. Extension rod 246 can be fixedly mounted onto first surface 240. Alternatively, shaft 242 disposed between gripping head 244 and handle 241 can be, but is not required to be, hollow for receiving holder extension 248. Extension rod 246 can extend through an aperture (not shown) on surface 244 to be received within shaft 242. In yet another alternative embodiment, first surface 250 can include a second rod extension 245. Second Rod extension 245 is adapted to receive first extension rod 246 therein so extension rod 246 is in communication with shaft 242.

Shaft 242 can include extension 243 for extending extension rod 246 through first surface 250. For example, the end of extension rod received within shaft 242 can include external threads that engage internal threads of extender 243. Twisting extender 243 caused extension rod to travel in a longitudinal direction parallel to the longitudinal axis 247 through shaft 242.

When the implants described in this present invention are inserted into a intervertebral space, the recessed areas defined by curved surfaces on the implants and the adjoining surfaces of the adjacent vertebra form a chamber or depot for osteogenic material. (See FIG. 11).

The recessed areas defined by curved surfaces of the implants described in the present invention can be packed with any suitable osteogenic material. The implants can be packed with osteogenic material prior to implantation or the osteogenic material may be inserted in to the chamber or depot in the intervertebral space after one or two of the implants have been inserted. In a preferred embodiment, the osteogenic composition substantially fills the recessed areas defined by the implants so that the osteogenic composition will contact the endplates of the adjacent vertebrae when the implant is implanted within the vertebrae. When "spongy" osteogenic material such as cancellous bone tissue is used, the cancellous tissue can be compressed into the recessed area or chamber to insure sufficient contact with adjacent endplates. This provides better contact of the composition with the endplates to stimulate bone ingrowth.

Any suitable osteogenic material or composition is contemplated, including autograft, allograft, xenograft, demineralized bone, and synthetic and natural bone graft substitutes, such as bioceramics and polymers, and osteoinductive factors. The terms osteogenic material or osteogenic composition used herein broadly include any material that promotes bone growth or healing including autograft, allograft, xenograft, bone graft substitutes and natural, synthetic and recombinant proteins, hormones and the like.

Autograft can be harvested from locations such as the iliac crest using drills, gouges, curettes and trephines and other tools and methods which are well known to surgeons in this field. Preferably, autograft is harvested from the iliac crest with a minimally invasive donor surgery. The osteogenic material may also include bone reamed away by the surgeon while preparing the end plates for the spacer.

Advantageously, where autograft is chosen as the osteogenic material, only a small amount of bone material is needed to pack the chamber. The autograft itself is not required to provide structural support as this is provided by the spacer. The donor surgery for such a small amount of bone is less invasive and better tolerated by the patient. There is usually little need for muscle dissection in obtaining such small amounts of bone. The present invention therefore eliminates or minimizes many of the disadvantages of employing autograft to provide structural support in the fusion procedure.

Natural and synthetic graft substitutes which replace the structure or function of bone are also contemplated for the osteogenic composition. Any such graft substitute is contemplated, including for example, demineralized bone matrix, mineral compositions and bioceramics. As is evident from a review of *An Introduction to Bioceramics*, edited by Larry L. Hench and June Wilson (World Scientific Publishing Co. Ptd. Ltd., 1993, volume 1), there is a vast array of bioceramic materials, including BIOGLASS®, hydroxyapatite, and calcium phosphate compositions known in the art which can be used to advantage for this purpose. That disclosure is herein incorporated by reference for this purpose. Preferred calcium compositions include bioactive glasses, tricalcium phosphates, and hydroxyapatites. In one embodiment, the graft substitute is a biphasic calcium phosphate ceramic including tricalcium phosphate and hydroxyapatite.

In some embodiments, the osteogenic compositions used in this invention comprise a therapeutically effective amount to stimulate or induce bone growth of a bone inductive or growth factor or protein in a pharmaceutically acceptable carrier. The preferred osteoinductive factors are the recombinant human bone morphogenetic proteins (rhBMPs) because they are readily available and do not contribute to the spread of infectious diseases. Most preferably, the bone morphogenetic protein is a rhBMP-2, rhBMP-4 or heterodimers thereof.

Recombinant BMP-2 can be used at a concentration of about 0.4 mg/ml to about 1.5 mg/ml, preferably near 1.5 mg/ml. However, any bone morphogenetic protein is contemplated including bone morphogenetic proteins designated as BMP-1 through BPM-13. BMPs are available from Genetics Institute, Inc., Cambridge, Massachusetts, and may also be prepared by one skilled in the art as described in U.S. Pat. Nos. 5,187,076 to Wozney et al.; 5,366,875 to Wozney et al.; 4,877,864 to Wang et al.; 5,108,922 to Wang et al.; 5,116,738 to Wang et al.; 5,013,649 to Wang et al.; 5,106,748 to Wozney et al.; and PCT Pat. Nos. WO93/00432 to Wozney et al.; WO94/26893 to Celeste at al.; and WO94/26892 to Celeste et al. All osteoinductive factors are contemplated whether obtained as above or isolated from bone. Methods for isolating bone morphogenetic protein from bone are described in U.S. Pat. No. 4,294,753 to Urist and Urist et al., 81 PNAS 371, 1984.

The choice of carrier material for the osteogenic composition is based on biocompatability, biodegradability, mechanical properties and interface properties as well as the structure of the load-bearing member. The particular application of the compositions of the invention will define the appropriate formulation. Potential carriers include calcium sulphates, polyactic acids, polyanhydrides, collagen, calcium phosphates, polymeric acrylic esters and demineralized bone. The carrier may be any suitable carrier capable of delivering the proteins. Most preferably, the carrier is capable of being eventually resorbed into the body. One preferred carrier is an absorbable collagen sponge marketed by Integra LifeSciences Corporation under the trade name Helistat® Absorbable Collagen Hemostatic Agent. Another preferred carrier is a biphasic calcium phosphate ceramic. Ceramic blocks are commercially available from Sofamor Danek Group, B.P. 4-62180 Rang-du-Fliers, France and Bioland, 132 Rou d Espangne, 31100 Toulouse, France. The osteoinductive factor is introduced into the carrier in any suitable manner. For example, the carrier may be soaked in a solution containing the factor. One preferred embodiment contemplates use of OSTEOFIL® allograph paste sold by Regeneration Technologies, Inc. The allograph paste can be supplemented with a local autograft obtained from the cutting operation.

The present invention also includes instrumentation for preparing the intervertebral space between adjacent vertebrae for receiving an implant and for inserting the implant into the prepared space. Use of the implants in accordance with the present invention restores the disc height, restores segmental alignment and balance, protects nerve roots, restores weight bearing to anterior surfaces, and immobilizes the unstable degenerated intervertebral disc area. The spacers of this present invention may be conveniently implanted with known instruments and tools although improved instruments are provided that are specifically adapted for the procedure. Any instrument that will firmly hold the implant and permit the implant to be inserted is contemplated. Preferably, the instrument will be adapted to compensate for the open structure of the spacers of this invention.

It is also provided with the present invention instruments for using and inserting the implants described herein. Specific instruments include box chisels, impact or slap hammers, shavers, retractors, detractors, scrapers such as round scrapers, plain scrapers, rotatable scrapers or cutters, toothed scrapers and bone loaders. In addition, there is provided a protective sleeve illustrated in FIG. 36 for use in guided surgical procedures.

Figures 25, 25A:
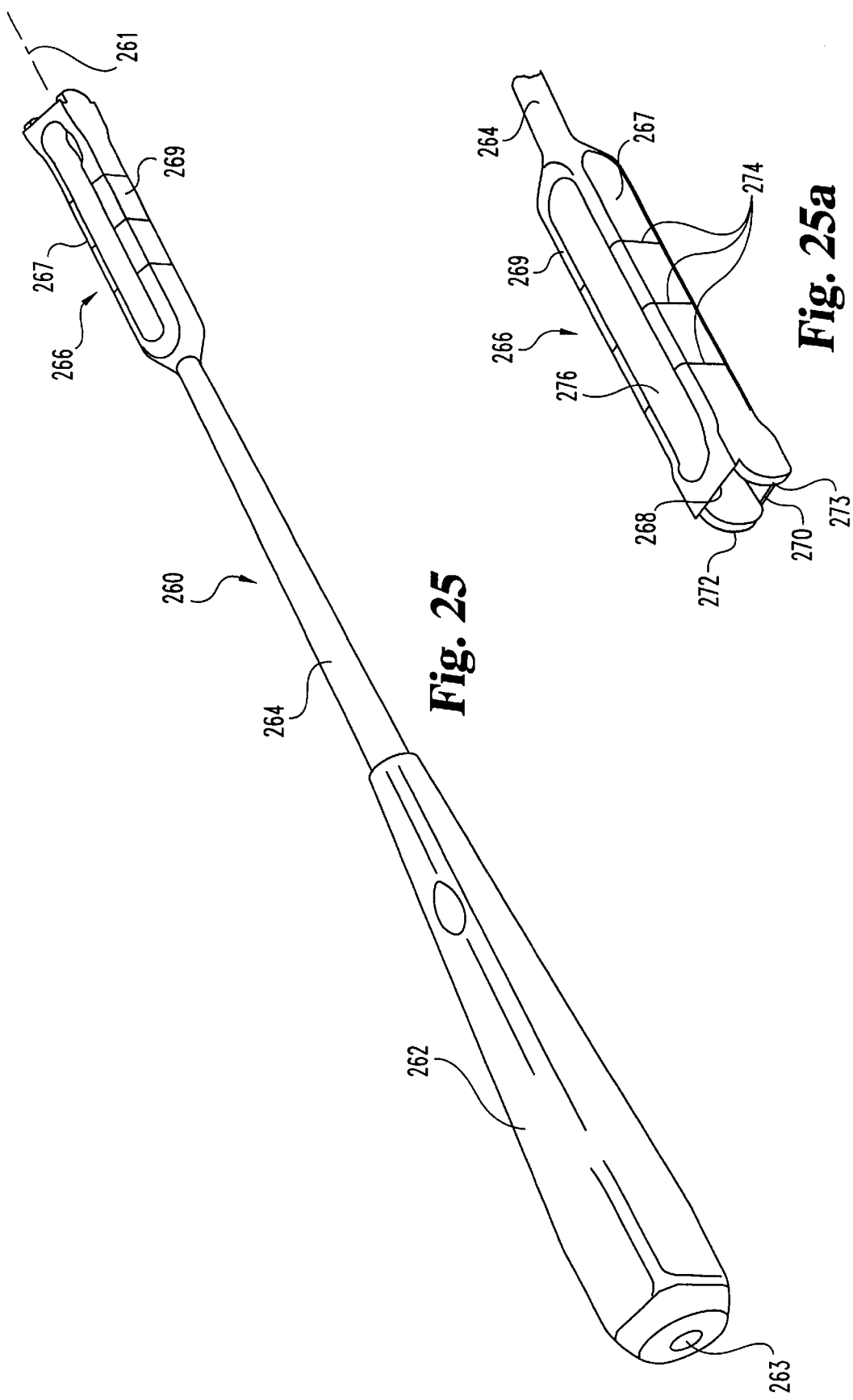
FIG. 25 is a perspective view of one embodiment of a chisel according to the present invention.
FIG. 25a is an enlarged perspective view of the cutting head of the chisel of FIG. 25.
Figure 25B:
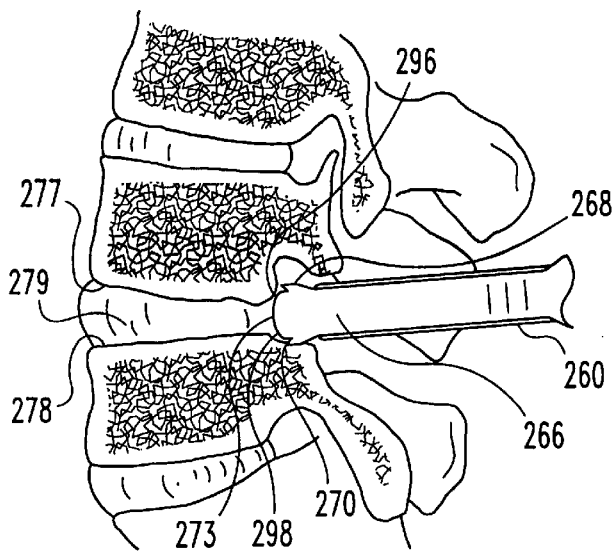
FIG. 25b is a side sectional view of three lumbar vertebrae and the chisel of FIG. 25 as it is initially inserted into the intervertebral space.
Figure 25C:
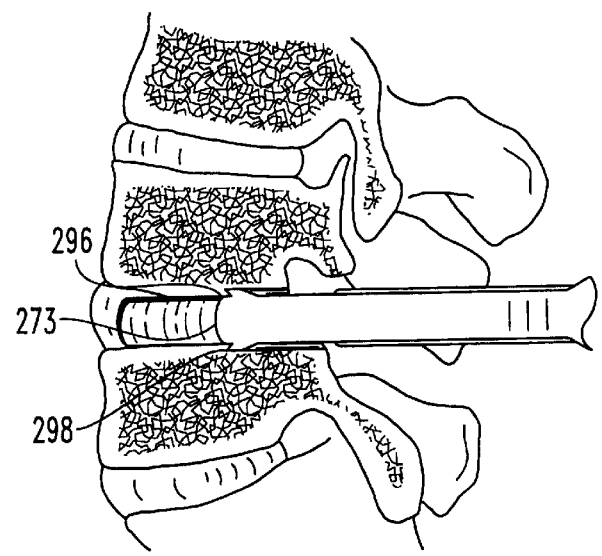
FIG. 25c is a side sectional view of three lumbar vertebrae and the chisel of FIG. 25 cutting the opposing surfaces of adjacent vertebrae.
Figure 25D:
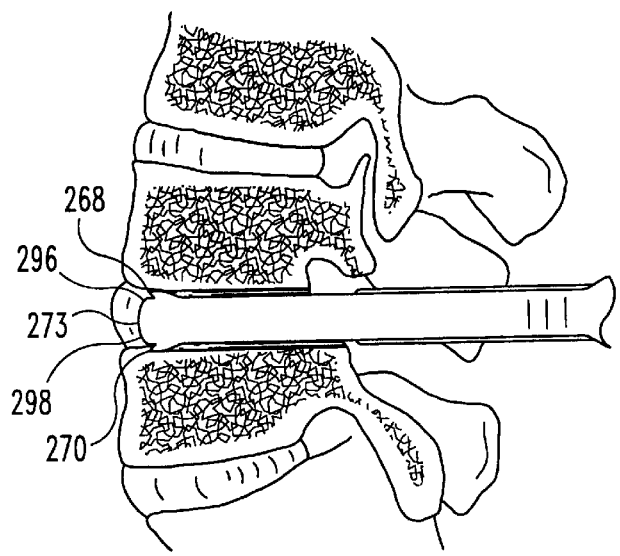
FIG. 25d is a side sectional view of three lumbar vertebrae and the chisel of FIG. 25 after completing the initial cavity formation in the intervertebral space.

In one aspect of the invention, a novel chisel is provided. The novel chisel for preparation of the preformed cavity in the intervertebral disc space is depicted in FIGS. 25 through 25d. Box chisel 260 includes a handle 262, having an engagement hole 263 adapted for attachment of an impacting tool such as a slap hammer shown in FIG. 27. In addition, box chisel 260 includes shaft 264 extending from handle 262 and connecting with cutting head 266. Shaft 264 defines a longitudinal axis 261. Cutting head 266 includes first arm 267 and opposing second arm 269 extending from shaft 264 substantially parallel to longitudinal axis 261. Upper cutting blade 268 and opposing lower cutting blade 270 are disposed between first and second arms 267 and 269. First arm 267 and second arm 269 define internal cavity 276 for receipt of bone chips and cutting debris. One or both of first arm 267 and second arm 269 include index markings 274, which indicate the depth of cut for the box chisel, thus allowing the surgeon to determine how deeply he/she has cut into the intervertebral space.

Non-cutting edge 273 is attached to first arm 267. Similarly, non-cutting edge 272 is attached to first arm 269. Non-cutting edges 273 and 272 are positioned to extend distally beyond cutting blades 268 and 270 in a direction parallel to the longitudinal axis. Referring to FIGS. 25b–c, non-cutting edge 273 includes an upper guide portion 296 and a lower guide portion 298 extending at least partially beyond the cutting edges. Similarly, non-cutting edge 272 includes identical upper and lower guiding portions. The guiding portions contact the surface prior to the cutting edges 268 and 269. Preferably the non-cutting edges 273 and 272 of the adjacent vertebrae are rounded to follow the interior surfaces of the opposing end plates of adjacent vertebrae. Thus, the rounded non-cutting edges follow along the surfaces of end plates and center the box cutter within the disc space and the included upper and lower cutting blades 268 and 270 between the two end plates. When the two cutting blades are centered between the opposing endplates, the blades cut equal amounts of bone from each end plate and are prevented from creating a potential offset opening between the endplates, resulting in improper implant placement and excess bone removal, which could increase the risk of implant interface subsidence.

Figure 27:
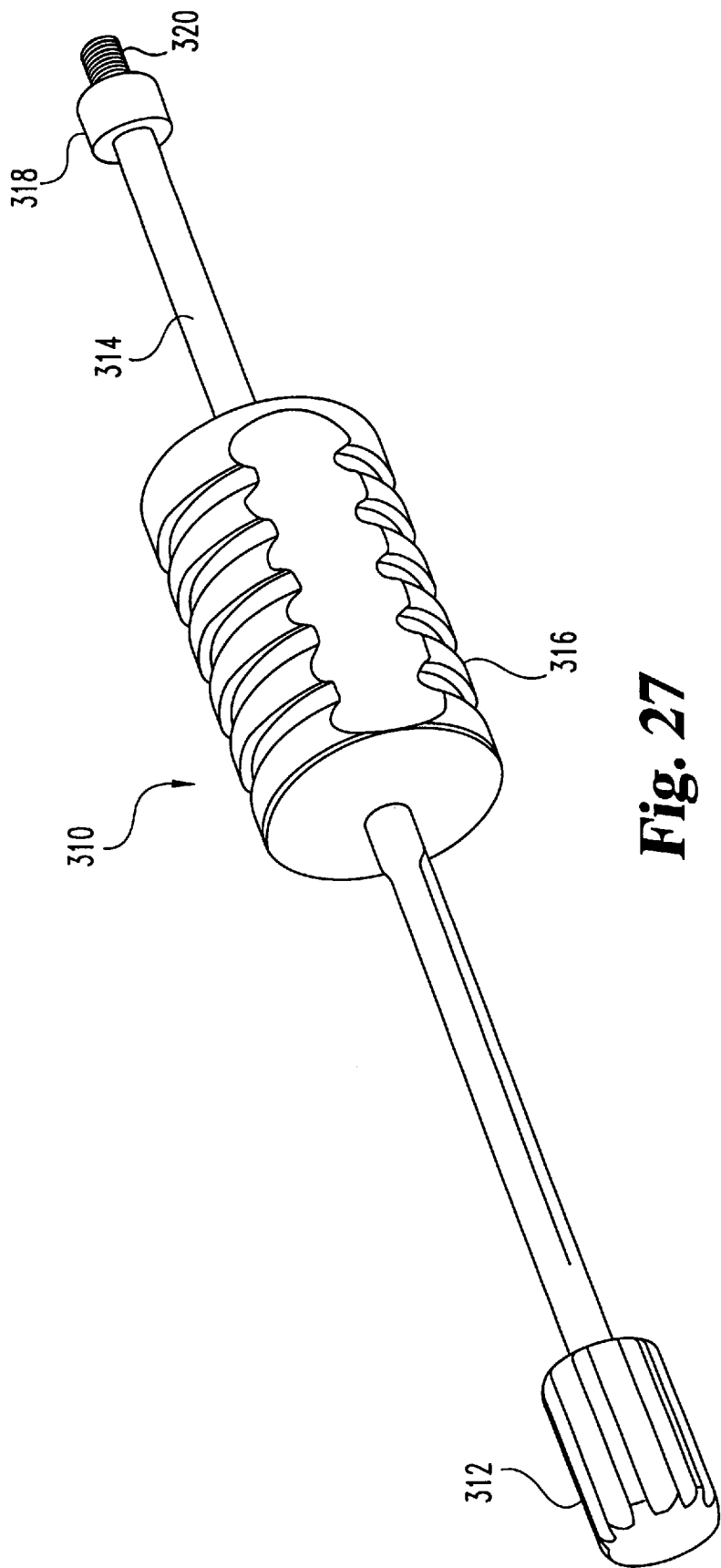
FIG. 27 is a perspective view of one embodiment of a slap hammer for use with the present invention.

Attachment hole 263 in handle 262 of box chisel 260 is provided for attachment of an impact or slap hammer as depicted in FIG. 27. Impact hammers are well known in the art and attachment hole 263 can be provided for attachment to any of the known impact hammers for use with the present invention. In preferred embodiments, slap hammer 310 includes threaded end 320. Threaded end 320 is threadedly engaged in internal threads in 263. Slap hammer 310 includes weight 316 that slides on shaft 314. Use of a slap hammer in accordance with this invention allows for controlled force impacting cutting tool and implants. The slap hammer also provides a means for removal of impacted surgical tools such as the chisel after cutting.

Referring now to FIGS. 25b–d, in use box chisel cutting head 266 is positioned in substantial alignment with a space 279 between adjacent vertebrae endplates 277 and 278. Non-cutting edges are inserted into space 279 with guiding portions 296 and 298 engaging endplates 277 and 278. Cutting head 266 is then advanced, by use of a slap hammer if necessary, with blades 268 and 270 removing the tissue of endplates 277 and 278, respectively, disposed between the guide portions and the blades.

Figure 28:
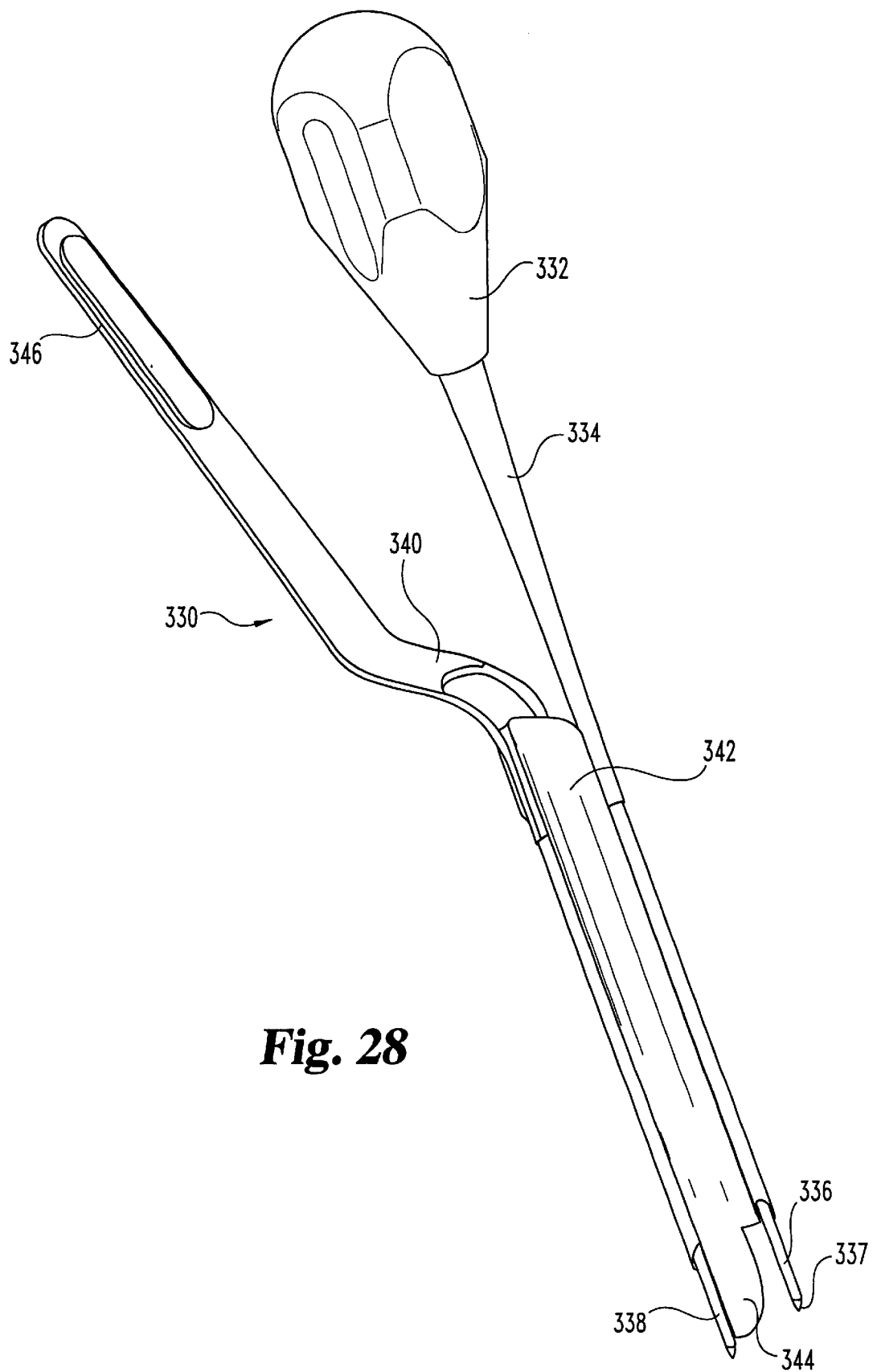
FIG. 28 is a perspective view of one embodiment of a nerve retractor assembly according to the present invention.
Figures 29, 29A:
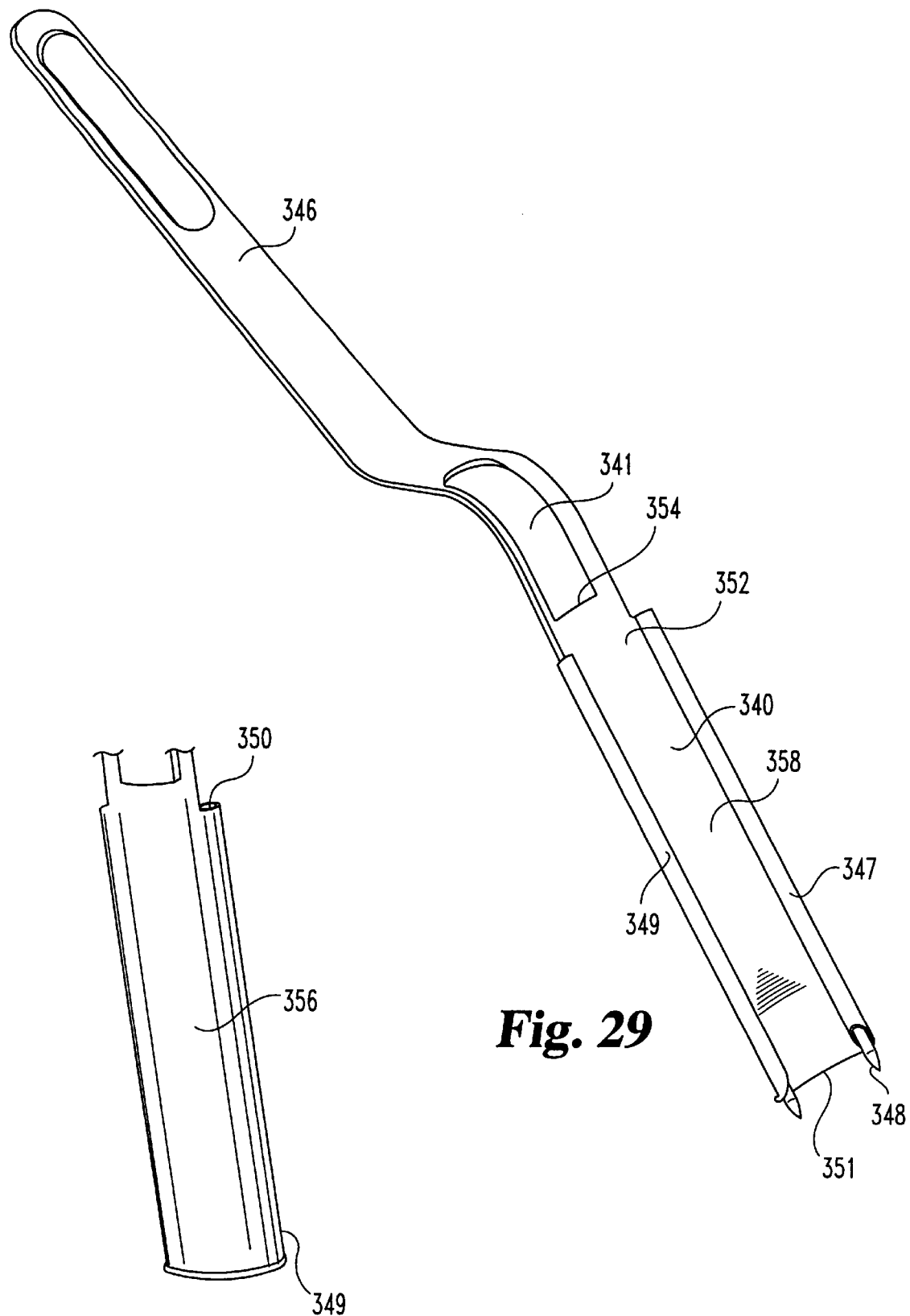
FIG. 29 is a perspective view of a retractor holder illustrated in FIG. 28.
FIG. 29a is a partial perspective view of the back of the support blade for the retractor of FIG. 29.

There is also provided in the present invention a novel retractor assembly as depicted in FIGS. 28–30. Nerve retractor assembly 330 includes retractor handle 346, retractor 340, and channel 352 for receiving retractor blade 342. Channel 352 of retractor 340 is provided in a shape to minimize the amount of retraction of the neural structure necessary to perform the procedures yet provide the surgeon with an unobstructed view of the intervertebral space. Channel 352 and retractor blade 342 are illustrated in FIGS. 28 and 30 as having a generally concave shape. It is also considered within the scope of the present invention to provide channel 352 and retractor blade 342 in alternative shapes to meet specific needs to gain access to a surgical site.

Nerve retractor assemble 340 also includes at least one, preferably two, supporting members positioned on opposing sides of channel 352. Preferably channel 352 includes at least one, preferably two, enlarged edges 347 and 349. Enlarged edges 347 and 349 can be adapted for receiving pin drive shaft 334. In addition, enlarges edges 347 are adapted to receive and hold retractor blade 342. Retractor blade 342 may be inserted from the top portion of channel 352 adjacent shoulder 354 and slidably advanced toward distal end 351. Blade 342 is retained in place by enlarged edges 347 and 349, as well as surface 358. Retainer blade 342 further includes a distractor tip 344 sized to be inserted into a disc space to achieve or maintain distraction. It will be understood that the width of tip 344 may be varied depending on the amount of distraction desired. Moreover, while pins 336 and 338 are disclosed for maintaining the position of the retraction assembly, it is contemplated that the engagement of retractor blade 342 in the disc space may be sufficient to hold the retraction assembly without the use of pins 337 and 338.

In alternative embodiments, pin 336 includes threads for threading engagement in internal threads (not shown) of supporting member 349. Thus, pin 336 can be anchored to the channel of retractor 340. Pin 336 includes pin driver handle 332, pin driver shaft 334, which can include a lower portion which is slidedly engaged in support member 350. Pin 336 includes at its distal end a tissue engagement end 337. A second pin 338 can be mounted on a second supporting member 350. After manipulation of the spinal structures using retractor blade 342 and retractor 340 to provide sufficient room to proceed with the PLIF operation, tissue engaging end 337 of pin 336 is forcibly inserted into tissue such as bone to secure the retractor blade and the retracted neural structures. Alternatively, the second pin 338 can be used to initially position and secure one side of nerve retractor assembly 330 relative to the nerve structure. After the pin has been used to secure one side of the retractor, the retractor can be used to engage and manipulate the selected nerve structure. After the nerve structure has be sufficiently retracted a second pin is forcibly inserted into tissue.

Retractor blade 342 is provided in a shape the can be nested in channel 352 to ensure that the surgeon has an unobstructed view of the surgical site. Retractor blade 344 includes lead ends of retractor 344 opposite stop 343. Stop 343 is inserted into opening 341 on retractor 340. Preferably stop 343 extends through opening 341 and engages shoulder 354 to secure retractor blade to retractor 340.

Figures 31, 31A:
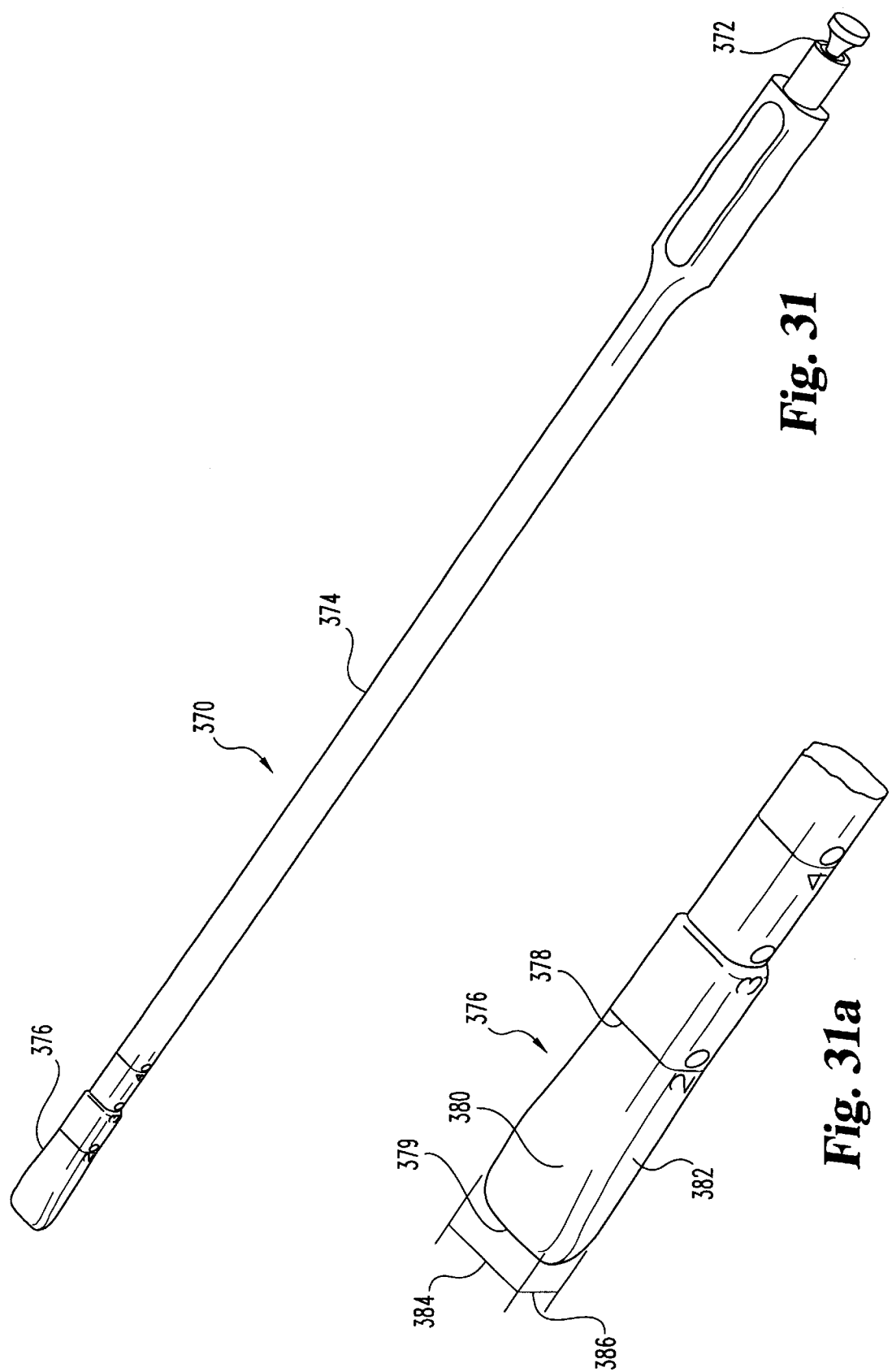
FIG. 31 is a perspective view of one embodiment of a distractor for use with the present invention.
FIG. 31a is a is a partial perspective view of the distractor tip of the distractor depicted in FIG. 31.

There is also provided in the present invention a distractor as depicted in FIGS. 31 and 31a. Distractor 370 includes coupling 372 attached to one end of shaft 374 and a distractor head 376 disposed opposite coupling 372 on shaft 374. Distractor head 376 is substantially in the form of a wedge shape, wherein distractor tip 379 forms the apex of the wedge. Preferably, distractor tip 379 contains a blunt edge. Distractor head 376 includes large side 380 and a corresponding large side opposite 380 to form the large side of a wedge. The large side of distractor head 376 is defined as having a length illustrated by reference line 384. Similarly, small side 382 and corresponding side opposite 382 form the short or small side of the wedge having a width illustrated by reference line 386. Furthermore, the detractor head includes a series of index markings 378 which index the depth the retractor is inserted into tissue.

Additional cutting instruments are provided for use with the present invention. For example, shaver 280 illustrated in FIG. 26 is provided with a cutting head 286, shaft 284, and handle 282. Handle 282 includes a receptacle 283 or attachment of a slap hammer. Cutting head 286 includes upper shaving blade 288 and lower shaving blade 290 provided between first arm 287 and second arm 289. Upper and lower shaving blade 288 and 290 are orthogonal to first and second arms 287 and 289 such that when the upper or lower shaving blade 288 or 290 or both are raked across tissue surfaces, the blades cut or scrape away a portion of tissue surface. Cutting head 286 also includes a series of index markings to determine the depth of the scraper head in tissue.

Round scraper illustrated in FIGS. 32–32f is provided for use with the present invention. Round scraper 390 includes shaft 402 and scraper head 392. Shaft 402 defines a longitudinal axis 391. Scraper head 392 includes a first arm 393 and a second arm 395. Shaft 402 includes a tapered neck 403. First arm 393 and second arm 395 define a cavity 398 for receipt of cutting debris. Attached to first and second arm 393 and 395 are rounded scraper edges 394 and 396. First arm 393 and second arm 395 are attached to curved tip 404. Rounded scraper edges 394 and 396 are backward-facing cutting edges, which can cut bone or other tissue as the round scraper 390 is withdrawn from the disc space Round scraper edges 394 and 396 are provided to allow simultaneous cutting on opposing surfaces of adjacent vertebral bodies. First arm 393 includes an upper surface 397 and a lower surface 400. Upper surface 397 and lower surface 400 are substantially flat. Second arm 395 includes similar structures. Upper surface 397 and/or lower surface 400 allow for controlled scaping of the disc space by contacting either the upper or lower vertebral body. Furthermore, the flat upper and lower surfaces 397 and 400 and tapered neck 403 are adapted to provide enhanced viewing of the disc space. It is important to be able to view the disc space while positioning the round scraper 390 in the disc space to remove bony tissue. Round scraper 390 is provided for preparing a bottom of the preformed cavity for proper seating of implants as depicted in the present invention.

There is also provided in accordance with the present invention a plane scraper 410 illustrated in FIGS. 33 through 33c. Plane scraper 410 includes scraper head 412. Scraper head 412 is adapted to provide a plurality of plane scraper blades 414 and 416. Plane scraper blades 414 and 416 are integrally attached to first arm 415 and second arm 417. One or both of first arm 415 and/or 417 include index markings 418 to indicate the depth the plane scraper is inserted into the cavity. First and second arm 415 and 4 17 define a cavity 420 for receipt of bone cuttings and debris.

Figure 34B:
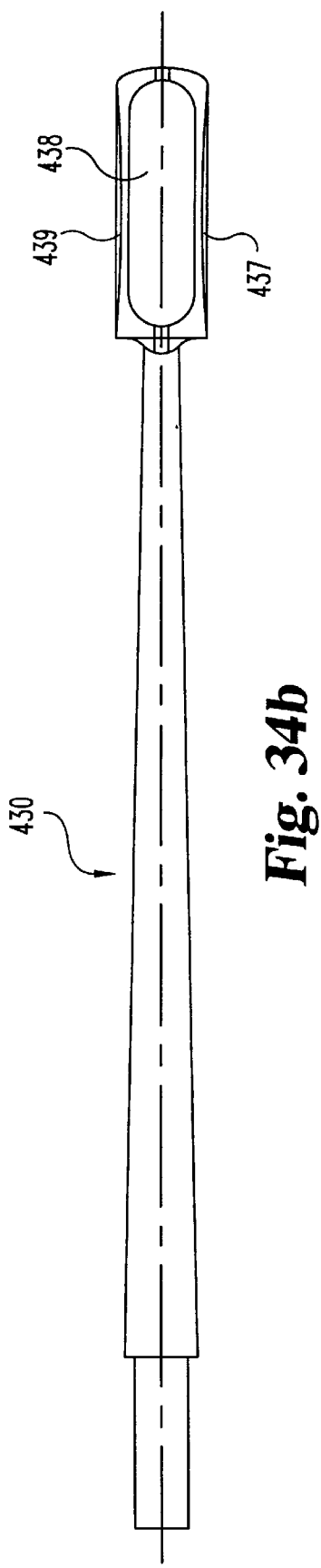
FIG. 34b is an elevated top view of the rotatable cutter of FIG. 34.
Figure 34C:
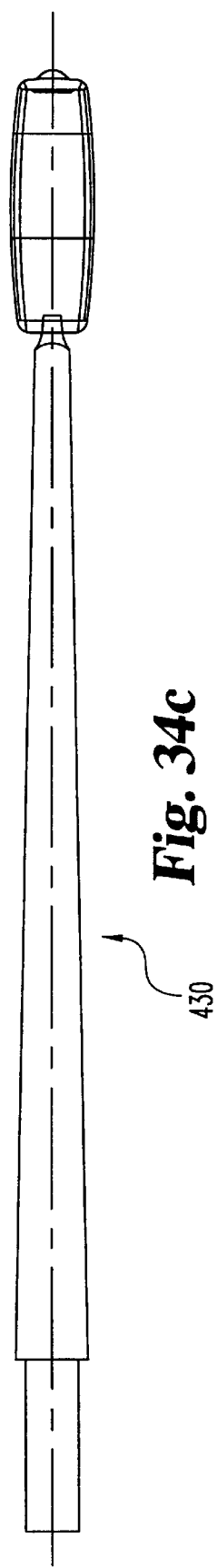
FIG. 34c is a side view of the rotatable cutter of FIG. 34.
Figure 34D:
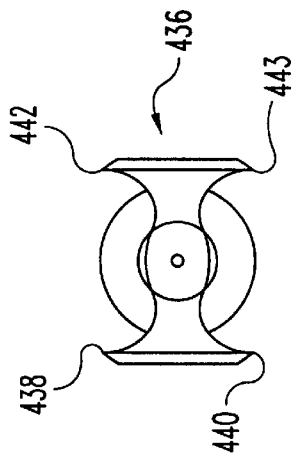
FIG. 34d is a first end view of the rotatable cutter of FIG. 34.

As shown in FIG. 34, there is also provided in accordance with the present invention rotatable cutter 430. Cutter 430 includes handle 432, shaft 434, and cutter head 436. Cutter head 436 includes first cutting arm 437 and second arm 439. First cutting arm 437 and second cutting arm 439 are spaced apart and define a cavity 448 therebetween for receipt of cutting debris. First cutting arm 437 includes at least two cutting blades. For example, FIG. 34a depicts cutting arm 437 having a first cutting blade 438 and opposite second cutting blade 440. First and second cutting blades extend longitudinally and are positioned to lie parallel to the longitudinal axis of rotatable cutter 430. Similarly, second cutting arm 439 is provided with a first cutting blade 442 and a second cutting blade 443. Rotatable cutter 430 is provided for use in a disc space to cut adjacent endplates of adjacent vertebrae by a twisting the cutter. As with other instruments the cutting head includes index marks 440 to 30 indicate the depth the rotatable cutter is inserted into tissue.

Referring to FIG. 35, also toothed scraper 460 is provided in accordance with the present invention. Toothed scraper 460 includes handle 462, shaft 464, shaped flat distal end 466, and cutting head 468. Cutting head 468 includes a plurality of scraper edges, each scraper edge having a series of teeth 471. In preferred embodiments, scraper head 468 includes first scraper edge 470 and second scraper edge 472. Scraper head 468 culminates in a curved distal end 474. As with other instruments provided in accordance with the present invention, cutting head 468 includes index markings 476 to indicate the depth the cutter is inserted into tissues.

Figure 36:
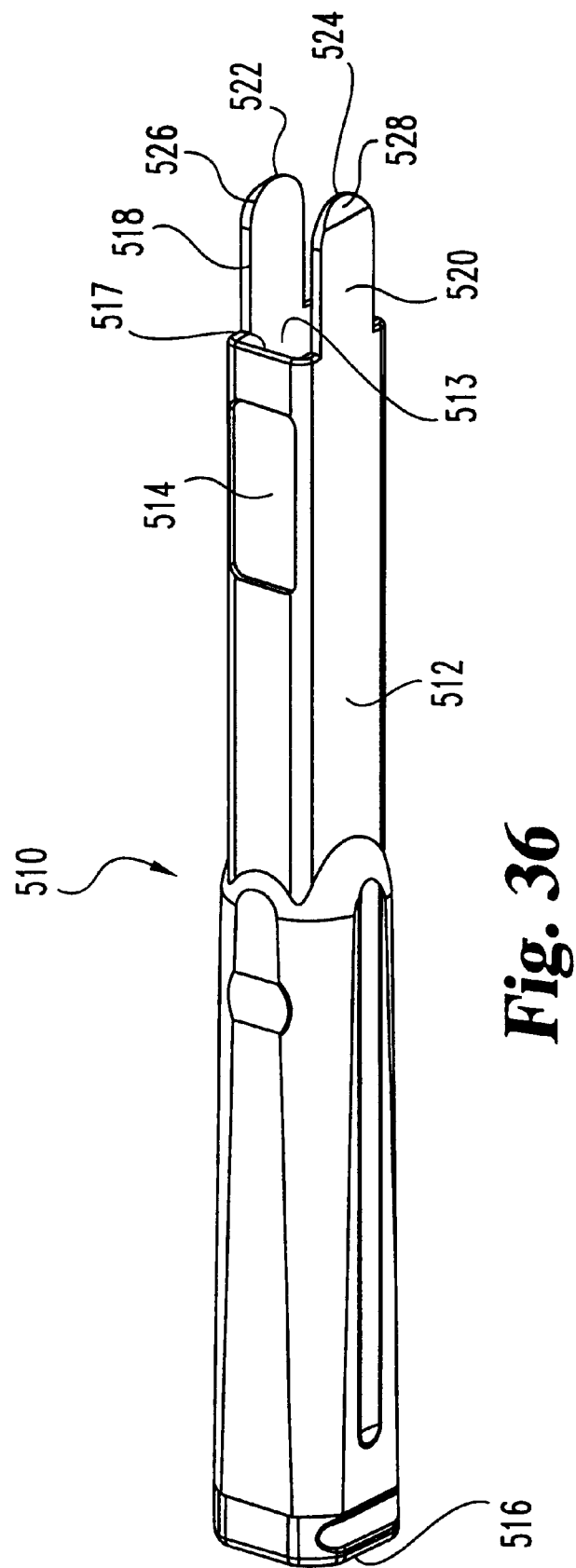
FIG. 36 is a perspective view of one embodiment of a guide sleeve for receiving surgical instruments and implantation instruments of the present invention.

A preferred embodiment of protective guide sleeve 5 10 is illustrated in FIG. 36. Protective sleeve 510 includes hollow body 512. In preferred embodiments, hollow body 512 is provided in the form of a hollow rectangular tube. Hollow body 512 includes a seating end 516, which is open and provides access to the interior of hollow body 512. Hollow body 512 also includes an opposite end that branches into a first distractor fin 518 and second distractor fin 520 extending from end 517. First distractor fin 518 is provided with inclined surface 526, which tapers to reduce the width of distractor fin 518. Distractor fin 518 furthermore culminates in a first curve tip 522. Second distractor fin 520 also includes an inclined surface 528 and culminates in curve tip 524. Positioned between the seating end 516 and first and second distractor fins 518 and 520 is viewing aperture 514. Viewing aperture 514 is provided for visualization of the interdisc space and viewing the index marks on the instruments that are inserted through the interior core of hollow body 512. Use of protective sleeve 510 allows a surgeon to minimize incised area and exposure of internal tissue during posterior lumbar interbody fusion surgical procedures. The protective sleeve 510 provides protection for neural structures. Furthermore, seating end 516 of protective sleeve 510 provides a surface for engaging depth stops on surgical instruments to control cutting bony surfaces and countersinking implants.

A number of surgical instruments are illustrated in FIGS. 37–40c that can be used in conjunction with guide sleeve 512. These instruments include many of the same features, benefits and aspects as have already been disclosed in the above description. In addition, these instruments include additional features and objects. These instruments are adapted to be received within the interior region of guide sleeve 512. In general, these surgical instruments include a shaft attached to a surgical head adapted to be received within the interior region of a guide sleeve.

Figure 38:
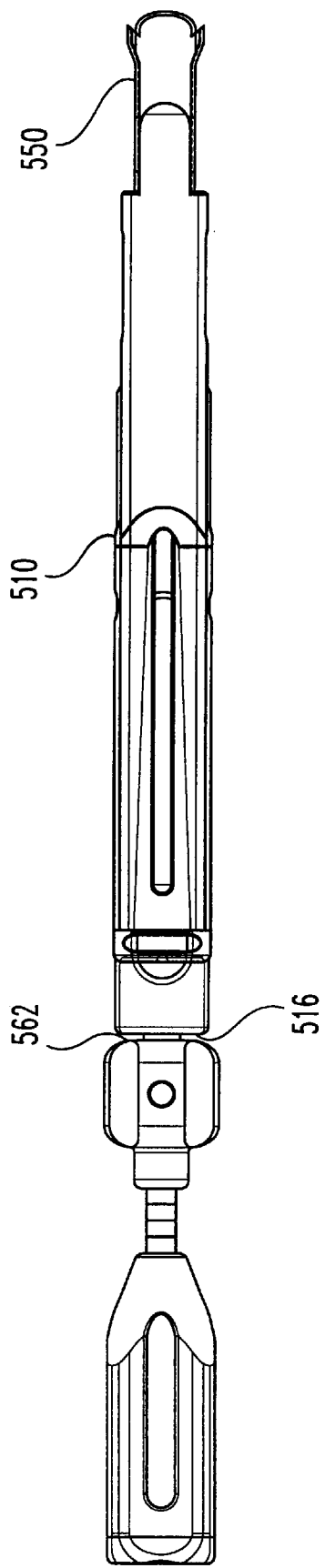
FIG. 38 is a side view of the chisel depicted in FIG. 37a received inside the guide sleeve depicted in FIG. 36.
Figure 39A:
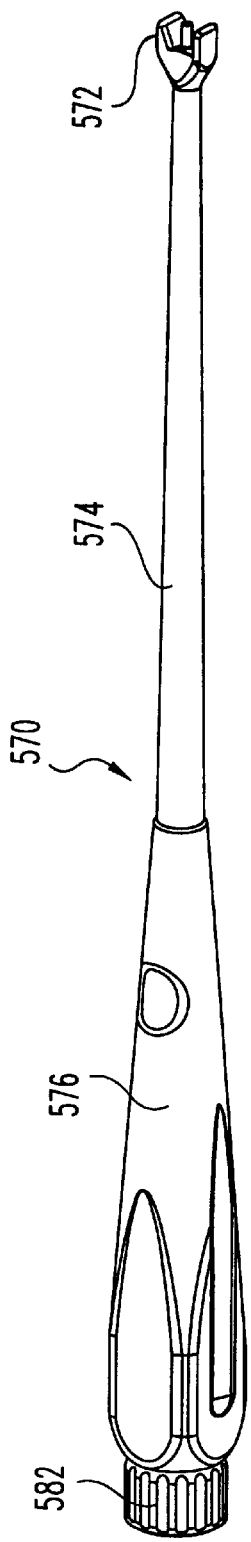
FIG. 39a is a perspective view of an alternative embodiment of an implant holder.
Figure 39B:
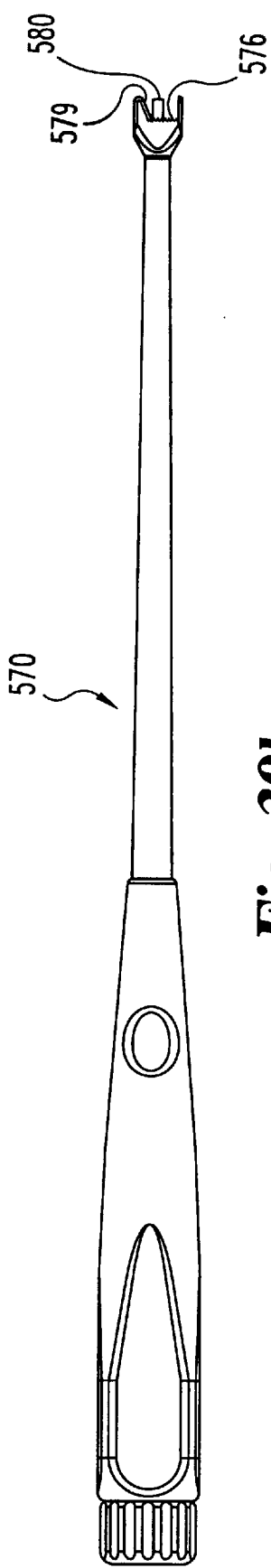
Figure 39C:
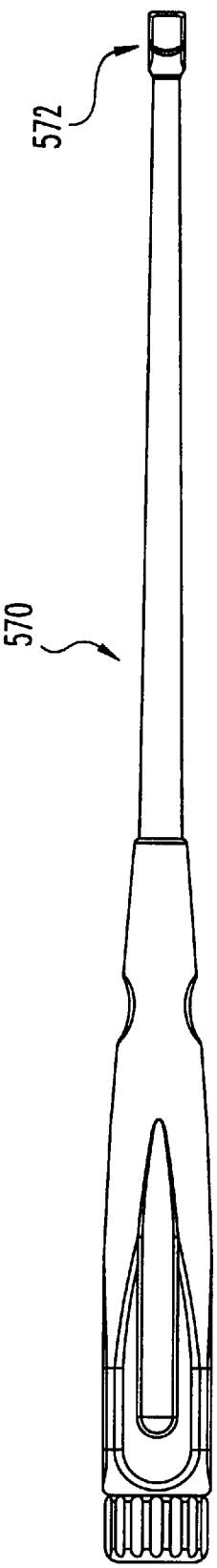
Figure 39D:
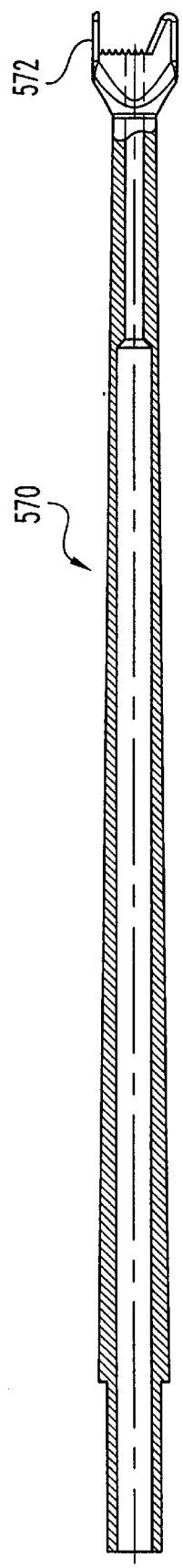
Figure 39F:
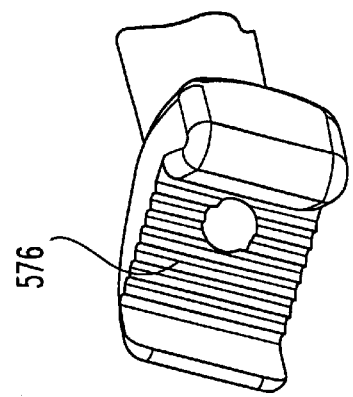
Figure 39E:
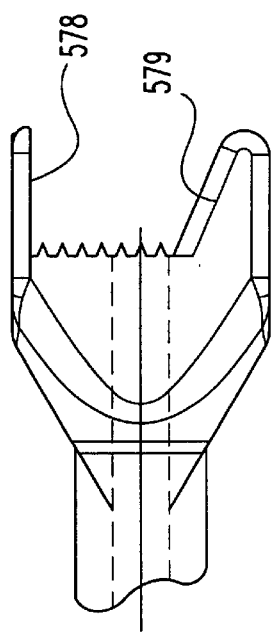

Yet another embodiment of a box chisel is illustrated in FIGS. 37a–38. Similar to the embodiment depicted in FIG. 25, Chisel 550 comprises a cutting head 551 that includes first non-cutting edge 554, second non-cutting edge 556 an upper cutting blade 558 and a lower cutting blade 560. Cutting head 551 includes internal cavity 557. Chisel 550 further includes a shaft 552 that is adapted to be received within the interior region 53 of protective guide sleeve 510 as illustrated in FIG. 38. Depth stop 562 is mounted on shaft 552 to prevent the chisel from cutting deeper than a predetermined depth by contacting seating end 516 on protective sleeve 510. In a preferred embodiment illustrated in FIG. 38, depth stop is threadedly mounted on shaft extension 564 so that rotation of depth stop 562 about the shaft adjusted the depth of cut. Depth indicator marks 566 on shaft extension 564 indicate the depth the chisel will cut when the depth stop 562 has contacted seating end 516.

Referring now to FIGS. 39a–39f, another embodiment of an implant holder is illustrated. The implant holder 570 includes a gripping head 572 shaft 574 and handle 576. As with other embodiments of the implant hold described for use with the present invention, implant holder 570 releaseably secures and impacts an implant into a preformed cavity. Gripping head 572 includes structural features for both securely gripping the implant and for driving the implant. For example, in the preferred embodiment illustrated in FIGS. 39e and 39f, gripping head includes a roughened impacting surface 576. Roughened impacting surface 576 is provided substantially orthogonal to the direction the implant is impacted into the vertebral body. The roughened surface provides frictional engagement with the tool engaging end of the implant and in combination with a second structure such as a second surface 578, inclined surface 579 or a shaft extension 580 secure the implant to the gripping head during the PLIF operation. Once the implant has been driven into the vertebra body, the implant is released from the gripping head.

Yet another embodiment of the implant holder is illustrated in FIGS. 40a–40c Implant holder 590 includes griping head 591, shaft 592, depth stop 593, and handle 594. Gripping head 591 includes an impacting surface 595. Preferably impacting surface 595 is roughened or knurled. Gripping head 591 also includes a second surface 597, which is substantially orthogonal to impacting surface 595. A third inclined surface 598 abuts opposite end of impacting surface 595 from second surface 597. Shaft extension 599 protrudes through impacting surface 595 to be received within shaft 592. Handle 594 includes shaft extender 600, which is rotatably mounted on handle 594. In preferred embodiments, shaft extender 599 extends through shaft 592 and handle 594 and includes external threads that are matingly received in internal threads on shaft extender 600. Gripping head 591 includes structural features for both securely gripping the implant and for driving the implant into intervertebral space. For example, impacting surface 595 in combination with a second surface 597 and/or incline surface 598 secure the implant to the gripping head. Preferably, shaft extension 599 matingly engages in a tool-engagement recess on an implant. In preferred embodiments, shaft extension 599 is radiopaque and extends through implant body to or through the insertion end. Radiopaque shaft extension 599 provides a means for viewing the seating of an implant during surgery via radiography.

Implant holder 590 can be used with protective guide sleeve 510. Gripping head 591 and shaft 592 can be adapted to be slidably received within the interior region 513 of guide sleeve 510. Depth stop 593 on implant holder 590 is adapted to engage or contact the seating end 516 on guide sleeve 510.

In one preferred embodiment, implant holder 590 includes shaft 592, which is provided with a square or rectangular cross-section and adapted to be matingly received with a square or rectangular protective guide sleeve. Mating engagement of implant holder 590 within protective sleeve 510 correctly centers implant holder 590 and a secured implant in the prepared vertebral space.

Depth stop 593 can be provided on shaft 592 in a fixed position or a variable position. Varying the position of depth stop 593 on shaft 593 allows for depth control during impaction of implant into the prepared vertebral space.

Figures 41, 42:
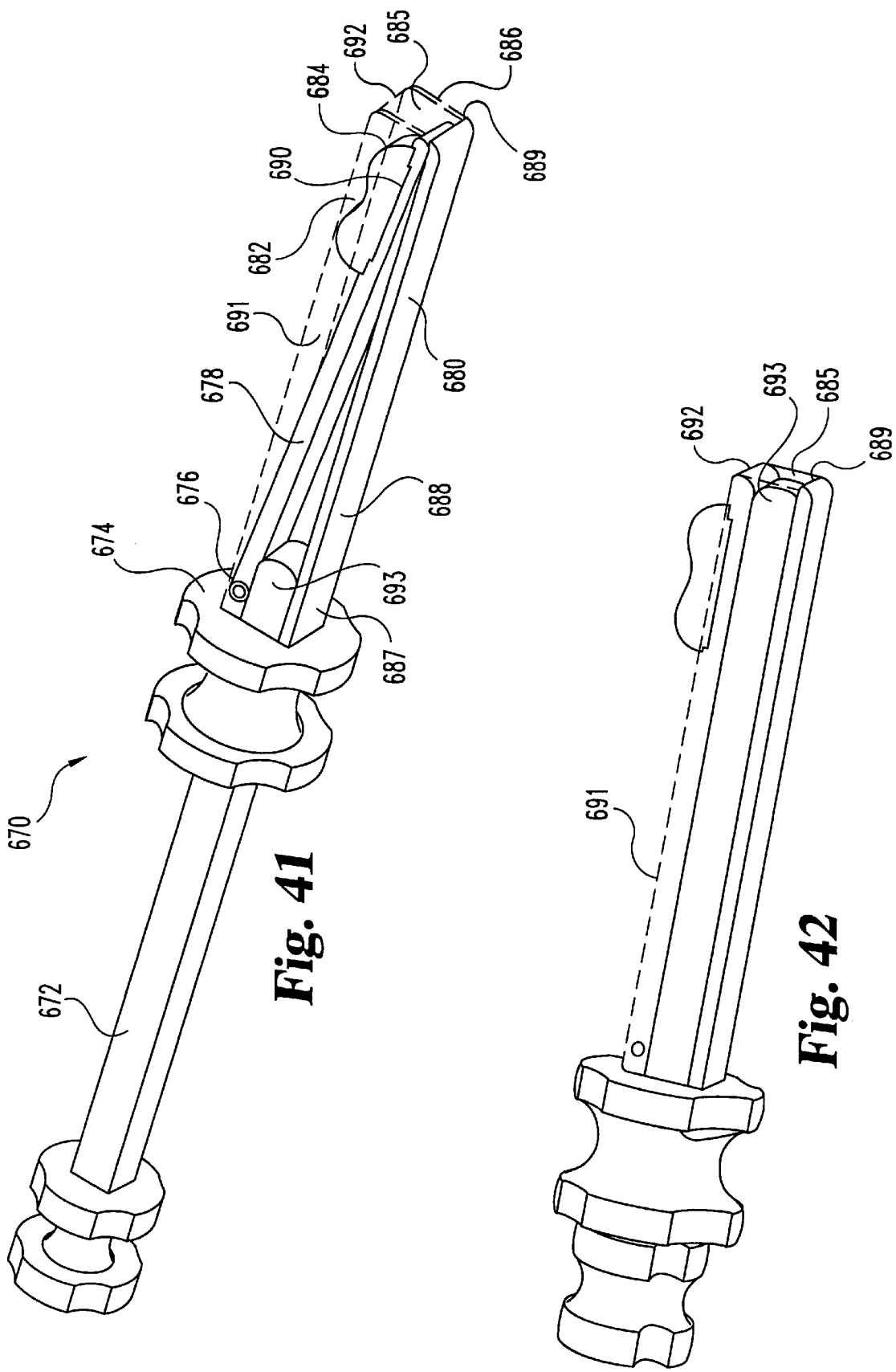
FIG. 41 is a perspective cutaway view of a bone graft loader according to the present invention.
FIG. 42 is a perspective cutaway view of the bone graft loader of FIG. 41 as the piston has been received in the loader shaft.

There is also provided in accordance with the present invention a bone graft loader 670 illustrated in FIGS. 41 and 42. Bone graft loader 670 includes plunger 672, depth stop 674, pivot plate 678 pivotally mounted with pivot pin 676 to loader shaft 680. Loader shaft 680 includes a first surface 688, a second bottom surface 689, an insertion end 686 and a second end 687. In preferred embodiments, loader shaft 680 also includes third wall 691, and fourth wall 692. Fourth wall 692 opposite first wall 688 includes opening 682 proximal to mounting surface 690 on pivot plate 678. Plunger 672 includes a first end 693 that is positioned within loader shaft 680. Furthermore, plunger 672 is adapted to be slidably received within loader shaft 680 such that plunger 672 is disposed between pivot pin 676 and first surface 688. In a first position first end. 693 of plunger 972 is proximal to depth stop 674 and disposed within loader shaft 680 between to pivot pin 676 and first wall 688. In a second position plunger 672 is proximal to insertion end 686 and within loader shaft 680 and disposed between pivot plate 678 and first wall 688. Pivot plate 678 is pivotally mounted to loader shaft 680 with pivot pin 676 and disposed within loader shaft 680 in a first position in a substantially a diagonal direction from pivot pin 676 to insertion end 686. In a second position pivot plate is disposed within loader shaft 680 to lie substantially parallel to fourth wall 692. Pivot plate 678 includes a mounting surface 690 for receiving osteogenic material 684. Opening 682 provides access to the interior of loader shaft 680 for receipt of osteogenic material, which can be deposited on mounting surface 690.

Figure 43A:
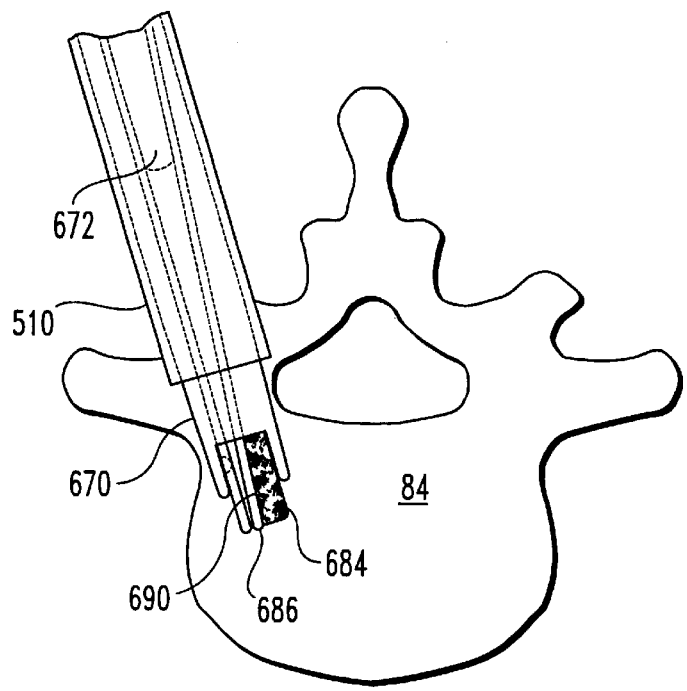
FIG. 43a is a cutaway view of an intervertebral space that includes a bone graft loader of FIG. 41 loaded with osteogenic material received within a protective sleeve and the intervertebral space.
Figure 43B:
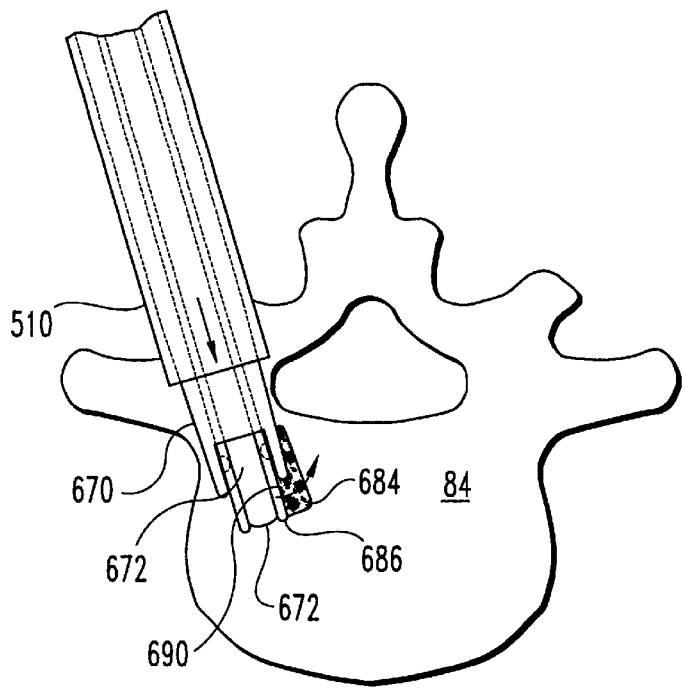
FIG. 43b is a cutaway view of an intervertebral space and the implant holder of FIG. 41 delivering osteogenic material into the intervertebral space.

Referring to FIGS. 43a and 43b. Bone loader 670 can be adapted to be slidably received within protective guide sleeve 510. Loader shaft 670 can be used to pack osteogenic material, such as morselized bone graft, into the intervertebral space. The morselized bone graft can be packed either prior to insertion of an implant or subsequent to insertion of an implant. Osteogenic material 684 is packed onto mounting surface 690 through opening 682 while plunger 672 is in a first position distal from insertion end 686 of shaft 680. Bone graft loader 670 is then inserted into guide tube 510 position insertion end 686 within the intervertebral space such that opening 682 opens either laterally or medially within the intervertebral space. Plunger 672 is pushed into loader shaft 680 in a direction toward insertion end 686. When plunger 672 is thus disposed within loader shaft 680, pivot plate 678 is disposed against fourth wall 692 and the osteogenic material 684 is forced through opening 682 and into the intervertebral space.

Bone graft loader 670 can also be used to anteriorly position osteogenic material in the intervertebral space. Plunger 672 is pushed part way into loader shaft 600 to dispose pivot plate 678 against fourth wall 692. Osteogenic material can be inserted into loader shaft 680 through opening 685 in insertion end 686. Insertion end 686 can be inserted into the disc space preferably through protective guide sleeve 510. Forcing plunger 672 fully into loader shaft 680 forces the osteogenic material into the disc space.

Reference to donor bone is understood, for the purposes of the present invention, to include cortical bone, cancellous bone, and any combination thereof, it being understood that cortical bone typically demonstrates greater structural integrity and is therefore a preferred material for fashioning load-bearing implants.

Implants prepared according to the present invention can include a portion of the exterior wall of a bone slice. In the J-shaped space superimposed on the bone slice 640, flat side 16 can include convex surfaces where flat side 16 abuts insertion end 17 and tool engagement end 32. The curvature results from providing bone 5 implants for the present invention through a more efficient use and conservation of donor bone. Bone implants such as dowels are formed from cross-sectional slices of long bones such as the femur, tibia and fibula. The remnants from this process include a curved surface formed from the outer walls of the bone slice. The most efficient use of these remnants may require that flat side 16 be machined to include at least a portion of the curved surface.

There also is provided a method of providing implants by a more efficient use of donor bone. Current methodologies for providing cortical bone infusion implant spacers typically require cutting the spacer, usually in the form of a dowel, from the diaphysis of a long bone. Only a certain portion of the diaphysis bone wall is sufficiently thick to provide dowels with requisite strength to maintain the intervertebral space. For example, in a human femur only about the middle third of the diaphysis, where the shaft is narrowest and the medullary canal is well formed, has sufficient thickness and density to be used to prepare cylindrical cortical dowels. The suitable portions of the diaphysis are sliced and then a cylindrical plug is cut from each slice.

Figure 46:
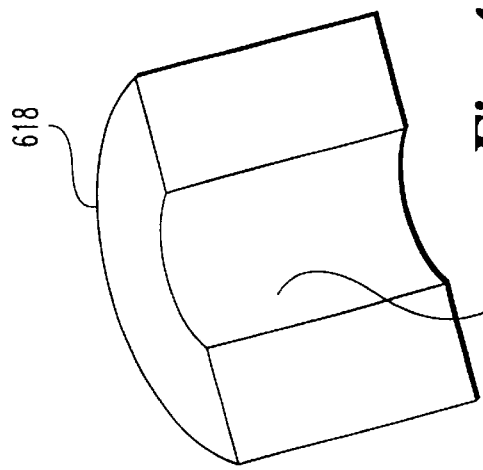
FIG. 46 is a perspective view of the bone remnant from FIG. 41b.
Figure 45:
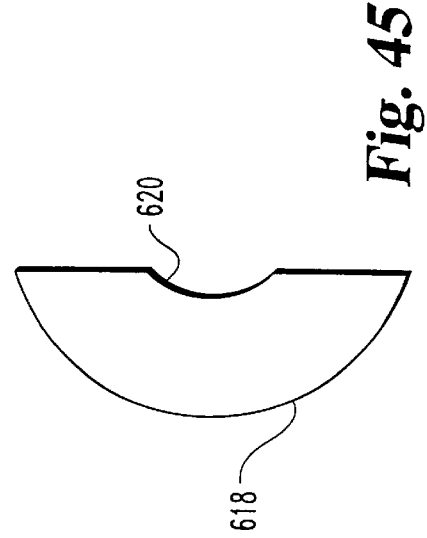
FIG. 45 is an elevated top view of the remnant of the bone section from FIG. 41b.
Figure 44C:
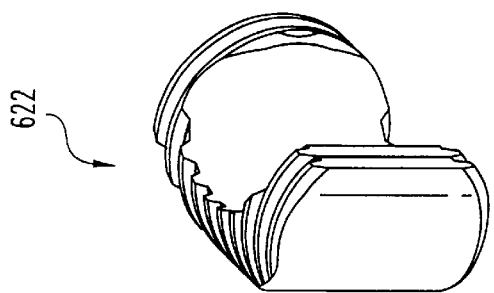
Figure 44A:
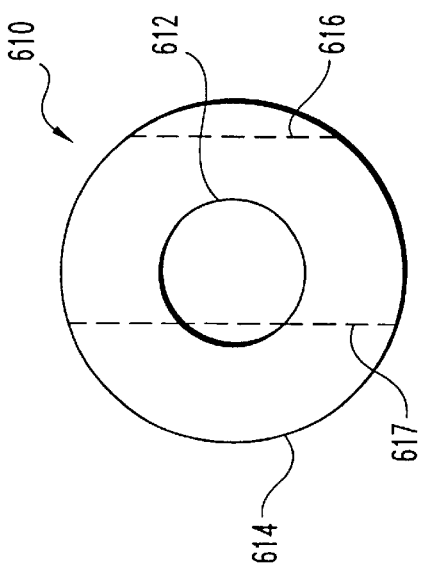
FIG. 44a is a top sectional view of an idealized diaphysis section of a long bone and the section needed for forming a cortical bone dowel.
Figure 44B:
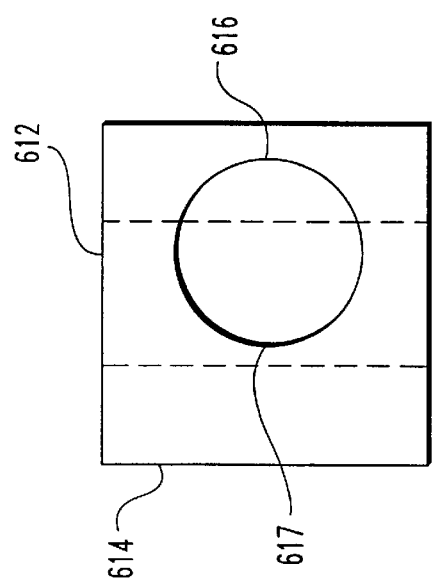
FIG. 44b is a side view of an idealized section from the diaphysis of a long bone indicating the medullary canal and the portion of the bone needed for forming a cortical bone dowel of the prior art.

FIG. 44a illustrates bone slice 610 viewed from above, which was cut from the diaphysis of a long bone. The medullary canal 612 lies substantially in the center of the bone slice. Reference lines 616 and 617, which outline a pattern for cylindrical dowel, are superimposed on bone slice 610. In FIG. 44b the bone slice 610 is viewed from the side, and pattern of the cylindrical bone dowel is defined by reference lines 616 and 617. The cylindrical bone dowels are cut from the bone slice then machined to form a cylindrical dowel having the desired shape and surface features. Most often the cylindrical dowels include the medullary canal to provide a depot for osteogenic material and promote fusion of the adjacent vertebrae. Much of the donor bone is wasted as is illustrated in FIGS. 45, 46 and 46a. Remnant 620, which includes a portion of the medullary canal 620 is often discarded. The present invention uses scraps such as remnant 620 to prepare implants. For example, remnant 620 may be used as a starting point to prepare a crescent shaped implant according to the present invention. In FIG. 46a a cortical bone dowel is illustrated. Cortical bone dowel 622 is formed from bone slice 610.

Figure 47:
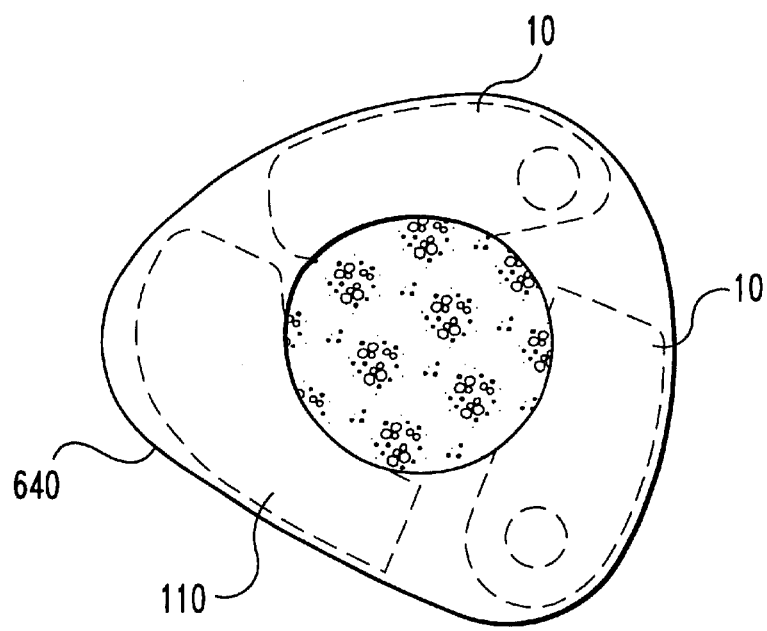
FIG. 47 is a top sectional view of an upper portion of the diaphysis of a humeral shaft.
Figure 48:
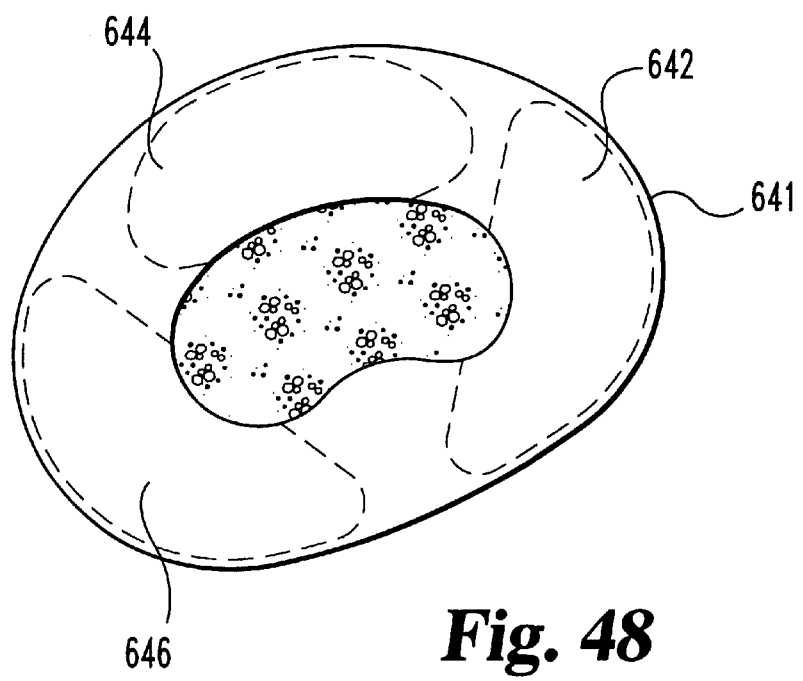
FIG. 48 is a top sectional view of an upper portion of the diaphysis of a tibial shaft.

Referring now to FIGS. 47 and 48, portions of long bones segments from the upper or lower third of the diaphysis of long bones are illustrated. Nearer to the end of the bone the slices are taken, the more irregular shaped the slices become. Cortical bone walls become much thinner or the medullary canal in these portions of the bone is not sufficient circular to be used to manufacture cylindrical dowels. The above-described bone segments are not suitable for the formation of cylindrical dowels. However, these segments of the long bones can be used to form the implants shaped according to the present invention. Moreover, utilization of the teaching of the present invention may yield a greater volume of implants from the same amount of donor bone. While it is within the scope of this invention to use any suitable long bone, FIGS. 47 and 48 illustrate sections of humeral and tibial shafts. In FIG. 47 bone slice 640 is illustrated. A J-shaped implant 110 and two implants 10 having flat sides are superimposed in bone slice 640. In a preferred embodiment, three J-shaped implants can be prepared from a single bone slice. Similarly, the bone segment of FIG. 48 may be divided into three crescent shaped implants. Crescent shaped implants 642, 644 and 646 are superimposed on bone slice.

Use of these previously undesirable donor portions in accordance with the present invention provides a more efficient use and conservation of a limited and very valuable resource of cortical donor bone.

The present invention also includes a method for fusing adjacent vertebrae. The patient is placed on the operating table in the prone position with lateral C-arm fluoroscopy. A midline incision provides the approach and exposure of the interlaminar space and facet joints at the affected level, which for this example is L4–5. The soft tissue exposure should also include the pedicle entry zone at L4 with care taken to not disrupt the facet caps or ligaments at L3–4. Exposure of the dura is accomplished in a routine fashion with bilateral hemi laminectomy and medial facetectomy with care to save the morselized bone ships removed during this decompression. After the lateral dura and nerve root traversing the L4–5 level has been exposed on both sides, the facet should be removed laterally so that there is an adequate exposure to the disc lateral to the L5 root bilaterally. An attempt to preserve some component of the L4–5 facet complex should be made if possible. The epidural veins are coagulated over the annulus or herniated disc and any tethering of the L5 root is dissected to allow for sufficient medial retraction of the dura and L5 root.

A conventional discectomy is performed by incising the annulus with preferably a 15 scalpel blade and removing this annulus with a discectomy rongeur. This is done bilaterally, and then soft fragments from the intradiscal space or extruded fragments are removed with the discectomy rongeur in a conventional fashion. Loose intradiscal fragments are removed both medially and laterally into a depth of about 30 mm.

The remaining soft tissue or cartilaginous endplate coverings are scraped away from the endplate using the round scraper 390. This vigorous scraping or curettage of the soft tissue endplate material is done starting medially under the midline and gradually working laterally in a sweeping motion until the upper and lower cartilaginous endplates have been cleared of the soft tissue. This is also performed bilaterally with the intent to create satisfactory endplate surface to promote fusion of the endplate and morselized graft to be inserted in the disc space later in the procedure.

The disc space is then sequentially distracted until the original disc space height is obtained and the normal foraminal opening accomplished. This is done by inserting a 9 or 10 mm distractor 370 on one side, rotating it, and then taking a distractor 370 1 mm larger and inserting it in the opposite side, rotating it, and then alternating sides until the desired height is obtained. The largest distractors are left in the disc space in the distracted position while continued disc space preparation is performed on the opposite side.

Rotating cutter 430 is inserted into the non-distracted side and rotated to remove residual intradiscal material and create a channel in the dorsal-most endplate, removing osteophytes and facilitating placement of the guide tube anchoring fins. The rotating cutter 430 is inserted into a depth of about 30 mm, rotated and carefully lifted out, removing the soft tissue from the disc space. After using this on the left side, the distractor 370 is removed from the right, inserted on the left, distracted, and then the rotating cutter 430 is used on the right side in the same fashion. This is inserted and rotated until there is no further soft tissue removed from the disc space. After removing the rotating cutter, the discectomy ronguers may also be re-inserted to remove residual soft tissue. At this point, the disc space and opening is ready to accept protective sleeve 510.

Using fluoroscopic guidance, appropriate size guide sleeve 510 is selected, and with the dura retracted using flat, bayoneted, dura and nerve root retractor, protective sleeve 510 is seated down into the laminectomy defect and first distractor fin 518 and second distractor fin 520 are anchored into the disc space. Using the mallet, the guide sleeve is then impacted securely into the laminectomy opening with caution not to trap dura or the upper traversing root under the protective sleeve end 517. Once this has been seated on the disc space and the seating confirmed using fluoroscopic guidance, distractor 370 is removed from the opposite side, and the nerve root retractor is lifted out as well.

The appropriate box chisel 550 is then inserted into the guide tube and with the slap hammer or the mallet is impacted down into the disc space, cutting the tract in the endplate to accept the bone graft. This is done using fluoroscopic guidance to ensure that the upper cutting blades 558 and lower cutting blades 560 enter the disc space and traverse in a parallel fashion to the endplates. The depth of the chisel may be adjusted by rotating depth 562 stop at the top of chisel 550. Once the chisel has been impacted to the desired depth, preferably about 23–28 mm, it is then removed using the slap hammer technique, carefully removing it from the disc space. After removal of the chisel, whose internal cavity 557 may also include disc and endplate material, the discectomy rongeur is inserted down the guide tube to remove any further residual soft tissue.

The side-loading morselized bone graft loader 670 is then loaded with an alloquat of morselized autologous or autograft bone and then inserted into the guide sleeve 510 with the side opening 682 aimed laterally. Once the bone graft loader 670 is fully inserted in the guide sleeve 510, the piston 672 is impacted down the loader shaft 680 delivering the morselized bone laterally. The bone graft loader 670 is then removed in this "delivered position," the piston removed from the loader shaft 680, and the second alloquat of bone inserted in the bone graft loader. The bone graft loader 682 is then again inserted and aimed with the opening 602 aimed medially. When fully inserted, an alloquat of morselized bone is then delivered medially under the midline. The bone graft loader is once again removed, and the disc space is ready to accept the structural allograft.

The appropriate-sized implant 210 is then attached to implant holder 570 and the shaft extension 580 is fully extended by turning extension knob 582, seating the graft on the loader firmly. It is then placed in the guide sleeve 510 and impacted into the disc space to the desired depth. The shaft extension 580 is then unscrewed from the graft and then implant holder 570. The guide sleeve 510 is also then removed from disc space and the discectomy and graft site inspected. The epidural space is then temporarily packed with gel foam for hemastasis, and the entire procedure is again repeated on the opposite side.

After the interbody grafts have been securely placed and their location confirmed using fluoroscopy, the large rongeur is used to remove the dorsal aspect of the L5 facet joint at the transverse process on the left side exposing the opening to the L5 pedicle. Using a pedicle probe and with fluoroscopic guidance, the trajectory or path of the pedicle is identified, the pedicle probe is removed, and the appropriatesized tap inserted down the pedicle, followed by the DYNA-LOK® pedicle screw. This same procedure is repeated at L4 with care taken not to disrupt the facet joint or ligament at L3–4. The lateral aspect of the facet and transverse process at the junction are removed with the rongeur followed by the probe, tap, and then pedicle screw. This is again repeated on the opposite side. When all four screws have been placed, the titanium plate is seated down over the pedicle screws. The residual morselized bone from the laminectomy and facet is packed laterally over the residual facet joint and medical transverse processes and then the locking screws are seated down onto the plate, and pedicle screws tightened to secure the plates to the pedicle screws. If necessary, a compressor is used to place compression forces on the pedicle screws as the nuts are being tightened down. After the nuts have been tightened, the epidural space is once again inspected for appropriate decompression of the L4 and L5 nerve roots, hemastatis is obtained using the gel foam sponge, and then the wound is closed in layers after irrigating with vast tracent solution. Care is taken to close the fascia securely and attach it to the residual spinous process and interspinous ligament if possible.

It is understood to those skilled in the art that the above procedure can be directed to a transforminal procedure using a far lateral PLIF approach through the facet joint. Typically the facet joint is removed to provide an approach to the disc space in an oblique orientation relative to the posterior vertebral body. This provides access. to the disc space with minimal retraction of the dural structure and nerve roots.

While the invention has been illustrated and described in detail in the drawings and the foregoing description, the same is considered to be illustrative and not restrictive in character. It is understood that only the preferred embodiments have been shown and described and that all changes and modifications that come within the spirit of the invention are desired to be protected.

We claim:

1. A chisel for cutting tissue from a first inferior surface of a first vertebrae and an opposing second superior surface of a second vertebrae adjacent to the first vertebrae, the chisel comprising:

a shaft having a first end and an opposite second end; and a cutting head mounted on the second end of the shaft, the cutting head including a first non-cutting edge attached to a first arm, a second non-cutting edge attached to an opposite second arm and a first cutting blade and a second cutting blade disposed between said first and second arms wherein said first non-cutting edge and said second non-cutting edge extend distally beyond said first and second cutting blades, thereby contacting the first inferior surface and the second superior surface to guide the first and second cutting blades.

2. The chisel of claim 1 wherein the cutting head further includes index marking determining the depth of cut.

3. The chisel of claim 1 wherein the shaft further includes a depth stop.

4. The chisel of claim 1 wherein the shaft is adapted to be slidably received within a guide sleeve.

5. The chisel of claim 1 wherein a cross section of the shaft is circular.

6. The chisel of claim 1 wherein a cross section of the shaft is rectangular.

7. A surgical kit comprising:

a chisel comprising a shaft having a first end defining a cutting head, the cutting head including a first non-cutting edge attached to a first arm, a second non-cutting edge attached to an opposite second arm and a first cutting blade and a second cutting blade disposed between said first and second arms wherein said first non-cutting edge and said second non-cutting edge extend distally beyond said first and second cutting blades;

a nerve retractor assembly comprising, a retractor blade; a retractor body adapted for unobstructed view of the retracted area wherein the retractor body is provided with a channel adapted to receive the retractor blade; and, a round scraper including an elongate shaft defining a longitudinal axis, said round scraper comprising a first arm extending from the shaft in a direction substantially parallel to the longitudinal axis, a second arm extending from the shaft and spaced from the first arm, wherein the first arm and the second arm define a cavity therebetween, and a tip disposed between the first arm and the second arm wherein the tip includes a first upper cutting edge and a second lower cutting edge and a curved surface disposed between the first cutting edge and the second cutting edge.

\* \* \* \* \*